United States Patent
Takeguchi et al.

(10) Patent No.: US 11,220,654 B2
(45) Date of Patent: *Jan. 11, 2022

(54) POWDERIZING AGENT FOR LIQUID COMPONENT

(71) Applicant: The Nisshin OilliO Group, Ltd., Tokyo (JP)

(72) Inventors: Seiya Takeguchi, Yokohama (JP); Yutaro Kataoka, Kanagawa (JP); Tetsuro Iwasawa, Yokohama (JP); Shin Arimoto, Yokohama (JP); Hidetaka Uehara, Yokohama (JP)

(73) Assignee: THE NISSHIN OILLIO GROUP, LTD., Tokyo (JP)

( * ) Notice: Subject to any disclaimer, the term of this patent is extended or adjusted under 35 U.S.C. 154(b) by 162 days.

This patent is subject to a terminal disclaimer.

(21) Appl. No.: 16/071,746

(22) PCT Filed: Jan. 20, 2017

(86) PCT No.: PCT/JP2017/001951
§ 371 (c)(1),
(2) Date: Jul. 20, 2018

(87) PCT Pub. No.: WO2017/126665
PCT Pub. Date: Jul. 27, 2017

(65) Prior Publication Data
US 2019/0031976 A1    Jan. 31, 2019

(51) Int. Cl.
| | | |
|---|---|---|
| C11B 15/00 | (2006.01) | |
| A23L 2/62 | (2006.01) | |
| A23L 2/50 | (2006.01) | |
| A61K 8/67 | (2006.01) | |
| A23L 2/38 | (2021.01) | |
| A23D 9/00 | (2006.01) | |
| A61K 8/37 | (2006.01) | |
| C11C 3/00 | (2006.01) | |
| C11C 3/02 | (2006.01) | |
| A23D 9/05 | (2006.01) | |

(52) U.S. Cl.
CPC ............... *C11B 15/00* (2013.01); *A23D 9/00* (2013.01); *A23D 9/05* (2013.01); *A23L 2/38* (2013.01); *A23L 2/50* (2013.01); *A23L 2/62* (2013.01); *A61K 8/37* (2013.01); *A61K 8/67* (2013.01); *C11C 3/00* (2013.01); *C11C 3/02* (2013.01); *A23V 2002/00* (2013.01)

(58) Field of Classification Search
CPC ... C11B 15/00; C11C 3/02; C11C 3/00; A23L 2/38; A23L 2/62; A23L 2/50; A23D 9/00; A61K 8/67; A61K 8/37
See application file for complete search history.

(56) References Cited

U.S. PATENT DOCUMENTS

| | | |
|---|---|---|
| 3,796,816 A | 3/1974 | Hasman et al. |
| 4,877,636 A | 10/1989 | Kovano et al. |
| 5,514,406 A | 5/1996 | Aoe et al. |
| 6,090,598 A | 7/2000 | Yamaguchi et al. |
| 8,535,749 B2 | 9/2013 | Kikuchi et al. |
| 9,695,384 B2 | 7/2017 | Schweitzer et al. |
| 2006/0115882 A1 | 6/2006 | Negishi et al. |
| 2008/0089981 A1 | 4/2008 | Butler et al. |
| 2010/0104694 A1 | 4/2010 | Schweitzer et al. |
| 2010/0278985 A1 | 11/2010 | Kikuchi et al. |
| 2011/0052771 A1 | 3/2011 | Rumbaut et al. |
| 2011/0200734 A1 | 8/2011 | Nosaka et al. |
| 2011/0223225 A1 | 9/2011 | Mezzenga et al. |
| 2011/0318453 A1 | 12/2011 | Suganuma et al. |
| 2013/0230634 A1 | 9/2013 | Arai et al. |
| 2016/0213020 A1 | 7/2016 | Oonishi |
| 2017/0208829 A1 | 7/2017 | Oonishi et al. |
| 2017/0267945 A1 | 9/2017 | Schweitzer et al. |
| 2018/0027838 A1 | 2/2018 | Suzuki et al. |

(Continued)

FOREIGN PATENT DOCUMENTS

| | | |
|---|---|---|
| CA | 2922936 A1 | 3/2015 |
| CN | 101909453 A | 12/2010 |

(Continued)

OTHER PUBLICATIONS

Apha F A C Gardner: "LOVIBOND 5.25 Cell Fatty Acid Specifications Typical Fatty Acid Composition % Packing", Nov. 19, 2008, XP055615791. (1 page).

(Continued)

*Primary Examiner* — Erik Kashnikow
*Assistant Examiner* — Assaf Zilbering
(74) *Attorney, Agent, or Firm* — Buchanan Ingersoll & Rooney PC

(57) ABSTRACT

Provided is means of powderizing a liquid component, wherein the powderizing agent contains an oil and/or fat composition, and when a total triglyceride content is set to 100% by mass, the oil and/or fat composition contains 65 to 99% by mass of one or more types of XXX-type triglycerides having fatty acid residues X, each with x carbon atoms, at positions 1 to 3 and 35 to 1% by mass of one or more types of X2Y-type triglycerides each having a fatty acid residue Y with y carbon atoms in place of one of the fatty acid residues X of the XXX-type triglyceride, x, the number of carbon atoms, is an integer selected from 8 to 20, and y, the number of carbon atoms, is each independently an integer selected from x+2 to x+12 and satisfies y≤22.

30 Claims, 6 Drawing Sheets

(56) References Cited

U.S. PATENT DOCUMENTS

| | | |
|---|---|---|
| 2018/0035688 A1 | 2/2018 | Oonishi et al. |
| 2018/0042259 A1 | 2/2018 | Oonishi et al. |
| 2018/0161301 A1 | 6/2018 | Nosaka et al. |
| 2018/0249729 A1 | 9/2018 | Kataoka et al. |
| 2018/0256531 A1 | 9/2018 | Nosaka et al. |
| 2019/0021355 A1 | 1/2019 | Takeguchi et al. |
| 2019/0021359 A1 | 1/2019 | Kataoka et al. |
| 2019/0029283 A1 | 1/2019 | Kataoka et al. |

FOREIGN PATENT DOCUMENTS

| | | | |
|---|---|---|---|
| CN | 102421883 A | 4/2012 | |
| CN | 103402364 A | 11/2013 | |
| CN | 106536696 A | 3/2017 | |
| CN | 107249344 A | 10/2017 | |
| CN | 107249346 A | 10/2017 | |
| CN | 107404893 A | 11/2017 | |
| CN | 108024550 A | 5/2018 | |
| DE | 28 32 636 A1 | 3/1980 | |
| EP | 0209327 A2 | 1/1987 | |
| EP | 0 536 824 B1 | 11/1995 | |
| EP | 1776870 B1 | 7/2011 | |
| EP | 2 622 966 A1 | 8/2013 | |
| EP | 2839750 A1 | 2/2015 | |
| EP | 3173464 A1 | 5/2017 | |
| EP | 3262948 A1 | 1/2018 | |
| EP | 3262949 A1 | 1/2018 | |
| GB | 879 211 A | 10/1961 | |
| GB | 1 316 079 A | 5/1973 | |
| GB | 1 564 363 A | 4/1980 | |
| GB | 1564363 A * | 4/1980 | ............ C11B 15/00 |
| JP | 52-071390 A | 6/1977 | |
| JP | 63-240745 A | 10/1988 | |
| JP | H-02-299544 A | 12/1990 | |
| JP | 03-287880 A | 12/1991 | |
| JP | 05-137506 A | 6/1993 | |
| JP | 06-033087 A | 2/1994 | |
| JP | 06-245700 A | 9/1994 | |
| JP | H-08-27 B2 | 1/1996 | |
| JP | 08-205773 A | 8/1996 | |
| JP | 3083967 B2 | 8/1996 | |
| JP | 2646422 B2 | 8/1997 | |
| JP | 2700377 B2 | 1/1998 | |
| JP | 10-295307 A | 11/1998 | |
| JP | 03083967 B2 | 9/2000 | |
| JP | 2002539782 A | 11/2002 | |
| JP | 2003135001 A | 5/2003 | |
| JP | 2005073610 A | 3/2005 | |
| JP | 2005-350660 A | 12/2005 | |
| JP | 2006-000087 A | 1/2006 | |
| JP | 2006-109731 A | 4/2006 | |
| JP | 3817450 B2 | 9/2006 | |
| JP | 2007236289 A | 9/2007 | |
| JP | 2007-289116 A | 11/2007 | |
| JP | 2009-249614 A | 10/2009 | |
| JP | 4352103 B2 * | 10/2009 | ............... C11C 3/10 |
| JP | 2012-157370 A | 8/2012 | |
| JP | 2012249617 A | 12/2012 | |
| JP | 5501764 B2 | 5/2014 | |
| JP | 2014124093 A | 7/2014 | |
| JP | 2014-212731 A | 11/2014 | |
| JP | 2015070837 A | 4/2015 | |
| WO | 2005005586 A1 | 1/2005 | |
| WO | 2008104381 A1 | 9/2008 | |
| WO | 2008123946 A1 | 10/2008 | |
| WO | WO 2010/052847 A1 | 5/2010 | |
| WO | 2011134627 A1 | 11/2011 | |
| WO | 2012043548 A1 | 4/2012 | |
| WO | 2012/169457 A1 | 12/2012 | |
| WO | 2014/069218 A1 | 5/2014 | |
| WO | 2014087724 A1 | 6/2014 | |
| WO | WO 2016/013582 A1 | 1/2016 | |

OTHER PUBLICATIONS

Ciftci et al.: "Formation of solid lipid microparticles from fully hydrogenated canola oil using supercritical carbon dioxide," Journal of Food Engineering, Barking, Essex, GB, vol. 178, Jan. 19, 2016, pp. 137-144, XP029431886.

Millqvist-Fureby: "Characterisation of spray-dried emulsions with mixed fat phases," Colloids and Surfaces. B, Biointerfaces, vol. 31, No. 1-4, Sep. 1, 2003, pp. 65-79, XP55614221, NL.

Nolen: "Biological Evaluation of Hydrogenated Rapeseed Oil," Journal of the American Oil Chemists' Society (JAOCS), vol. 58, No. 1, Jan. 1, 1981, pp. 31-37, XP55614258, DE.

International Search Report (PCT/ISA/210) and the Written Opinion of the International Searching Authority Form PCT/ISA/237) dated Mar. 7, 2017, by the Japanese Patent Office in the International Application No. PCT/JP2017/001952. (7 pages).

International Search Report (PCT/ISA/210) and the Written Opinion of the International Searching Authority (Form PCT/ISA/237) dated Mar. 7, 2017, by the Japanese Patent Office in the International Application No. PCT/JP2017/001953. (10 pages).

International Search Report (PCT/ISA/210) and the Written Opinion of the International Searching Authority Form PCT/ISA/237) dated Mar. 7, 2017, by the Japanese Patent Office in the International Application No. PCT/JP2017/001954. (9 pages).

The extended European Search Report dated Aug. 30, 2019, by the European Patent Office in European Patent Application No. 17741544.5. (7 pages).

The extended European Search Report dated Sep. 9, 2019, by the European Patent Office in European Patent Application No. 17741543.7. (8 pages).

The extended European Search Report dated Jan. 24, 2020, by the European Patent Office in European Patent Application No. 17741545.2. (11 pages).

The First Office Action dated Apr. 8, 2020, by the State Intellectual Property Office of People's Republic of China in Chinese Patent Application No. 201780007637.5, and an English translation of the Office Action. (21 pages).

Office Action dated Jun. 14, 2017, by the Japanese Patent Office in Japanese Patent Application No. 2017-522697. (2 pages).

Office Action (First Office Action) dated Apr. 28, 2020, by the State Intellectual Property Office of People's Republic of China in Chinese Patent Application No. 201780007669.5 and an English Translation of the Office Action. (17 pages).

International Search Report (PCT/ISA/210) dated Oct. 27, 2015, by the Japanese Patent Office as the International Searching Authority for International Application No. PCT/JP2015/070850.

Written Opinion (PCT/ISA/237) dated Oct. 27, 2015, by the Japanese Patent Office as the International Searching Authority for International Application No. PCT/JP2015/070850.

International Search Report (PCT/ISA/210) dated Dec. 6, 2016, by the Japanese Patent Office as the International Searching Authority for International Application No. PCT/JP2016/078122.

Written Opinion (PCT/ISA/237) dated Dec. 6, 2016, by the Japanese Patent Office as the International Searching Authority for International Application No. PCT/JP2016/078122.

International Search Report (PCT/ISA/210) dated May 10, 2016, by the Japanese Patent Office as the International Searching Authority for International Application No. PCT/JP2016/055420.

Written Opinion (PCT/ISA/237) dated May 10, 2016, by the Japanese Patent Office as the International Searching Authority for International Application No. PCT/JP2016/055420.

International Search Report (PCT/ISA/210) dated May 10, 2016, by the Japanese Patent Office as the International Searching Authority for International Application No. PCT/JP2016/055421.

Written Opinion (PCT/ISA/237) dated May 10, 2016, by the Japanese Patent Office as the International Searching Authority for International Application No. PCT/JP2016/055421.

International Search Report (PCT/ISA/210) dated May 10, 2016, by the Japanese Patent Office as the International Searching Authority for International Application No. PCT/JP2016/055422.

Written Opinion (PCT/ISA/237) dated May 10, 2016, by the Japanese Patent Office as the International Searching Authority for International Application No. PCT/JP2016/055422.

(56) References Cited

OTHER PUBLICATIONS

Extended Search Report dated Nov. 23, 2017, by the European Patent Office in European Patent Application No. 15824376.6 (9 pages).
Communication pursuant to Article 94(3) EPC issued by the European Patent Office in European Patent Application No. 15824376.6-1105 dated Jan. 8, 2019 (6 pages).
Extended Search Report issued by the European Patent Office in European Patent Application No. 16755552.3-1106 dated Jul. 17, 2018 (8 pages).
Extended Search Report issued by the European Patent Office in European Patent Application No. 16755551.5-1105 dated Sep. 20, 2018 (9 pages).
Communication pursuant to Article 94(3) EPC issued by the European Patent Office in European Patent Application No. 16755551.5-1105 dated Aug. 23, 2019 (5 pages).
Extended Search Report issued by the European Patent Office in European Patent Application No. 16755550.7-1105 dated Aug. 6, 2018 (9 pages).
Extended Search Report issued by the European Patent Office in European Patent Application No. 16848698.3-1106 dated May 22, 2019.
The First Office Action issued by The State Intellectual Property Office of People's Republic of China in Chinese Patent Application No. 201580040036.5 dated Mar. 28, 2010 (17 pages including partial English translation).
Office Action dated Dec. 25, 2019, by the State Intellectual Property Office of the People's Republic of China in Chinese Patent Application No. 201680012188.9 and an English translation of the Office Action. (17 pages).
First Office Action dated Feb. 27, 2020, by The State Intellectual Property Office of People's Republic of China in Chinese Patent Application No. 201680012214.8, with an English translation of the Office Action. (17 pages).
Amir et al., "Interesterification of fats and oils—A Review". Pak. J. Food Sci., 22(3), pp. 143-153. (Year: 2012).
Ishikawa et al., "Polymorphic Behavior of Palm Oil and Modified Palm Oils", Food Science and Technology International, (Jan. 1, 1997), vol. 3, No. 1, pp. 77-81, XP002716821.
Kebakile, "The Production of a High Free-Fat Whole Milk Powder for the Chocolate Industry The Spray Chilling Technology" Thesis, Massey University (1996) (111 pages).
Lipp et al.: "Review of cocoa butter and alternative fats for use in chocolate—Part A. Compositional data," Food Chemistry, Elsevier Ltd, NL, vol. 62, No. 1, Jan. 1, 1998, pp. 73-97.
Office Action issued by the U.S. Patent and Trademark Office in U.S. Appl. No. 15/553,906, dated Mar. 30, 2020, U.S. Patent and Trademark Office, Alexandria, VA. (18 pages).
Office Action issued by the U.S. Patent and Trademark Office in U.S. Appl. No. 15/553,640, dated Jun. 26, 2020, U.S. Patent and Trademark Office, Alexandria, VA. (8 pages).
Office Action issued by the U.S. Patent and Trademark Office in U.S. Appl. No. 15/327,734, dated Sep. 6, 2019, U.S. Patent and Trademark Office, Alexandria, VA. (8 pages).
Office Action issued by the U.S. Patent and Trademark Office in U.S. Appl. No. 15/553,771, dated Sep. 16, 2020, U.S. Patent and Trademark Office, Alexandria, VA. (8 pages).
Office Action issued by the U.S. Patent and Trademark Office in U.S. Appl. No. 15/553,640, dated Nov. 1, 2019, U.S. Patent and Trademark Office, Alexandria, VA. (8 pages).
Office Action issued by the U.S. Patent and Trademark Office in U.S. Appl. No. 15/553,906, dated Aug. 30, 2019, U.S. Patent and Trademark Office, Alexandria, VA. (17 pages).
Office Action issued by the U.S. Patent and Trademark Office in U.S. Appl. No. 15/553,906, dated Sep. 22, 2020, U.S. Patent and Trademark Office, Alexandria, VA. (23 pages).
Office Action issued by the U.S. Patent and Trademark Office in U.S. Appl. No. 16/071,796, dated Apr. 2, 2020, U.S. Patent and Trademark Office, Alexandria, VA. (7 pages).
Office Action issued by the U.S. Patent and Trademark Office in U.S. Appl. No. 16/071,796, dated Oct. 7, 2020, U.S. Patent and Trademark Office, Alexandria, VA. (9 pages).
Office Action issued by the U.S. Patent and Trademark Office in U.S. Appl. No. 16/071,830, dated Oct. 7, 2020, U.S. Patent and Trademark Office, Alexandria, VA. (9 pages).
Extended Search Report issued by the European Patent Office in corresponding European Patent Application No. 17741542.9-1105 dated Aug. 14, 2019 (6 pages).
Office Action dated Oct. 20, 2020, by the U.S. Patent and Trademark Office in U.S. Appl. No. 15/762,971. (10 pages).
Ribeiro et al., "Crystallization modifiers in lipid systems," Journal of Food Science and Technology, Jul. 2015, vol. 52, No. 7, pp. 3925-3946.
Yang et al., "Refined cottonseed oil as a replacement for soybean oil in broiler diet," Food Science and Nutrition, Feb. 2019, vol. 7, No. 3, pp. 1027-1034.
International Search Report (PCT/ISA/210) dated Mar. 7, 2017, by the Japanese Patent Office as the International Searching Authority for International Application No. PCT/JP2017/001951.
Written Opinion (PCT/ISA/237) dated Mar. 7, 2017, by the Japanese Patent Office as the International Searching Authority for International Application No. PCT/JP2017/001951.
Office Action dated Jun. 14, 2017, by the Japanese Patent Office for Application No. 2017-522695.
Japanese Patent Office Publication, Hyoujun Gijutsu-Shu, 2006 (Flavors), 2-2 Processing Techniques for Flavors, 2-2-2 Powders and Granules, Published on Mar. 14, 2007, pp. 328-330 (4 pages including partial English translation).
Communication pursuant to Article 94(3) EPC dated May 11, 2021, by the European Patent Office in European Patent Application No. 16755551.5. (5 pages).
Office Action dated Jun. 8, 2021, by the U.S. Patent and Trademark Office in U.S. Appl. No. 15/553,906. (10 pages).
Office Action dated Feb. 3, 2021, by the U.S. Patent and Trademark Office in U.S. Appl. No. 15/553,640. (11 pages).
Office Action dated Mar. 12, 2021, by the U.S. Patent and Trademark Office in U.S. Appl. No. 15/762,971. (7 pages).
Office Action dated Mar. 18, 2021, by the U.S. Patent and Trademark Office in U.S. Appl. No. 15/553,771. (8 pages).
Office Action dated Apr. 1, 2021, by the U.S. Patent and Trademark Office in U.S. Appl. No. 16/071,734. (12 pages).
Office Action dated Apr. 1, 2021, by the U.S. Patent and Trademark Office in U.S. Appl. No. 16/071,796. (7 pages).
Office Action dated Apr. 1, 2021, by the U.S. Patent and Trademark Office in U.S. Appl. No. 16/071,830. (7 pages).
Notice of Allowance dated Sep. 27, 2021, by the U.S. Patent and Trademark Office in U.S. Appl. No. 16/071,734. (9 pages).
Notice of Allowance dated Aug. 4, 2021, by the U.S. Patent and Trademark Office in U.S. Appl. No. 15/762,971 (9 pages).
Notice of Allowance dated Oct. 1, 2021, by the U.S. Patent and Trademark Office in U.S. Appl. No. 16/071,796. (9 pages).
Notice of Allowance dated Oct. 1, 2021, by the U.S. Patent and Trademark Office in U.S. Appl. No. 16/071,830. (9 pages).

* cited by examiner

Example 1  Example 2  Example 3

Example 4  Example 5  Example 6

Example 7  Example 8  Example 9

Example 10  Example 11  Example 12

Example 13   Example 14   Example 15

Example 16   Example 17   Example 18

Example 19   Example 20   Example 21   Example 22   Example 23

Example 24   Example 25   Example 26

Example 27  Example 28  Example 29

Example 30  Example 31  Example 32

Example 33    Example 34    Example 35

Example 36    Example 37    Example 38

POWDERIZING AGENT FOR LIQUID COMPONENT

TECHNICAL FIELD

The present invention relates to, for example, a powderizing agent for a liquid component and a method of producing a powder composition using the powderizing agent.

BACKGROUND ART

Products such as foods and/or beverages, cosmetics, and pharmaceutical drugs are blended with various functional materials.

Many of these products contain functional materials as liquid components, such as liquid foods, liquid cosmetics, and liquid-filled capsules. Because of the liquid form, when blended in products such as foods and/or beverages, these liquid components often face up to a limitation in terms of the amount blended and also difficulty in the blending method.

In light of the above, conventional techniques powderize the liquid components. Powderization not only improves miscibility into products but also contributes to the improvement of the storage stability and instant solubility of functional materials. For these reasons, powderization of liquid components provides great advantages (Non Patent Literature 1).

Here, for example, known methods of powderizing a liquid component include a method including adding an emulsifier, maltotriose, and water to an oil-soluble component to prepare an emulsified mixture and then spray drying this emulsified mixture (Patent Literature 1).

Instead of the spray drying method, known methods also include a method including heating and melting an oil and/or fat having a high melting point and then powderizing the liquid component by a spray cooling method (Patent Literature 2).

CITATION LIST

Patent Literatures

Patent Literature 1: Japanese Patent Application Publication No. 2006-87
Patent Literature 2: Japanese Patent Application Publication No. 2014-212731

Non Patent Literature

Non Patent Literature 1: Japanese Patent Office Publication, Hyoujun Gijutsu-Shu, 2006 (Flavors), 2-2 Processing Techniques for Flavors, 2-2-2 Powders and Granules, Published on Mar. 14, 2007

SUMMARY OF INVENTION

Technical Problems

However, there is a problem that since a heating operation is performed in the spray drying method, a heat sensitive liquid component evaporates or deteriorates due to oxidation, for example.

In addition, the spray cooling method requires a dedicated apparatus for flow rate control or high speed rotation and further requires a high level of expertise of the operator.

The present inventors identified the problems described above and further recognized that it was necessary to develop a method which makes it possible for anyone to easily powderize even a heat sensitive liquid component without the necessity of a special apparatus or skills.

Solution to Problems

The present inventors have made earnest studies on the above problems to find that use of an oil and/or fat composition containing a triglyceride having a particular structure in a particular composition makes it possible for anyone to easily powderize functional materials, conventionally used in the liquid form, by a process simpler than conventional ones. The present invention has been made based on this finding.

To be more specific, the present invention relates to the following:

[1] A powderizing agent for a liquid component, wherein
the powderizing agent contains an oil and/or fat composition, and
when a total triglyceride content is set to 100% by mass, the oil and/or fat composition contains
65 to 99% by mass of one or more types of XXX-type triglycerides having fatty acid residues X, each with x carbon atoms, at positions 1 to 3 and
35 to 1% by mass of one or more types of X2Y-type triglycerides each having a fatty acid residue Y with y carbon atoms in place of one of the fatty acid residues X of the XXX-type triglyceride,
x, the number of carbon atoms, is an integer selected from 8 to 20, and
y, the number of carbon atoms, is each independently an integer selected from x+2 to x+12 and satisfies y≤22.

[2] The powderizing agent according to [1] described above, wherein
the oil and/or fat composition is in a powder form.

[3] The powderizing agent according to [1] or [2] described above, wherein
the liquid component contains a hydrophobic substance.

[4] The powderizing agent according to any one of [1] to [3] described above, wherein
the liquid component is a solution of a hydrophobic substance.

[5] The powderizing agent according to [4] described above, wherein
a solvent of the solution is selected from the group consisting of liquid oils, alcohols, organic solvents, and mixtures thereof.

[6] The powderizing agent according to any one of [1] to [3] described above, wherein
the liquid component an emulsion of a hydrophobic substance.

[7] The powderizing agent according to [6] described above, wherein
the emulsion of a hydrophobic substance contains at least one selected from the group consisting of water, emulsifiers, and glycerin.

[8] The powderizing agent according to any one of [3] to [7] described above, wherein
the hydrophobic substance is selected from the group consisting of flavors, dyes, vitamins, lipids, and mixtures thereof.

[9] The powderizing agent according to [1] or [2] described above, wherein
the liquid component contains a hydrophilic substance.

[10] The powderizing agent according to [1], [2], or [9] described above, wherein
the liquid component is a solution of a hydrophilic substance.

[11] The powderizing agent according to [10] described above, wherein
a solvent of the solution is selected from the group consisting of water, alcohols, organic solvents, and mixtures thereof.

[12] The powderizing agent according to [1], [2], or [9] described above, wherein
the liquid component is an emulsion of a hydrophilic substance.

[13] The powderizing agent according to [12] described above, wherein
the emulsion of a hydrophilic substance contains at least one selected from the group consisting of water, emulsifiers, and glycerin.

[14] The powderizing agent according to any one of [9] to [13] described above, wherein
the hydrophilic substance is selected from the group consisting of flavors, dyes, vitamins, and mixtures thereof.

[15] The powderizing agent according to any one of [1] to [14] described above, wherein
the liquid component is a liquid form food.

[16] The powderizing agent according to [15] described above, wherein
the liquid form food is selected from the group consisting of cow's milk, wines, fruit juices, stock, and yogurts.

[17] A method of producing a powder composition, comprising:
a mixing step of mixing the powderizing agent according to any one of [1] to [16] described above and a liquid component.

[18] The production method according to [17] described above, further comprising a cooling step of cooling a mixture of the powderizing agent and the liquid component.

[19] The production method according to [17] or [18] described above, wherein
a seeding process, a tempering process, and/or a pre-cooling process are further performed between the mixing step and the cooling step.

[20] The production method according to any one of [17] to [19] described above, wherein
the liquid component contains a hydrophobic substance, and
an amount of the liquid component used is 0.1 to 30% by mass relative to a total mass of the powder composition.

[21] The production method according to any one of [17] to [19] described above, wherein
the liquid component contains a hydrophilic substance, and
an amount of the liquid component used is 0.1 to 300% by mass relative to a total mass of the powderizing agent.

[22] A powder composition produced by the production method according to any one of [17] to [21] described above.

[23] A powder composition comprising the powderizing agent according to any one of [1] to [16] described above.

[24] The powder composition according to [22] or [23] described above for use as a raw material or an intermediate of a product.

[25] The powder composition according to any one of [22] to [24] described above, wherein
the product is selected from the group consisting of foods and/or beverages, cosmetics, quasi drugs, pharmaceutical drugs, household goods, feeds, general goods, agricultural chemicals, and industrial chemical products.

[26] A food and/or beverage comprising the powder composition according to any one of [22] to [25] described above.

[27] The food and/or beverage according to [26] described above, being a luxury food.

[28] A method of powderizing a liquid component, comprising a step of mixing the powderizing agent according to any one of [1] to [16] described above and a liquid component.

[29] The method according to [28] described above, further comprising a cooling step of cooling a mixture of the powderizing agent and the liquid component.

[30] A powder composition powderized by the method according to [28] or [29] described above.

Advantageous Effects of Invention

As shown in Examples to be described later, a powderizing agent of the present invention can powderize functional materials, conventionally used in the liquid form, by a process simpler than conventional ones. In addition, since excessive heating is unnecessary in the powderization in accordance with the present invention, it is possible to powderize even a heat sensitive liquid component without the necessity of a special apparatus or skills.

Thus, the present invention can provide a product which is excellent in handleability at the time of manufacturing the product and in consumer convenience at the time of using the product.

DESCRIPTION OF EMBODIMENTS

<Powderizing Agent for Liquid Component>

Figure 1:
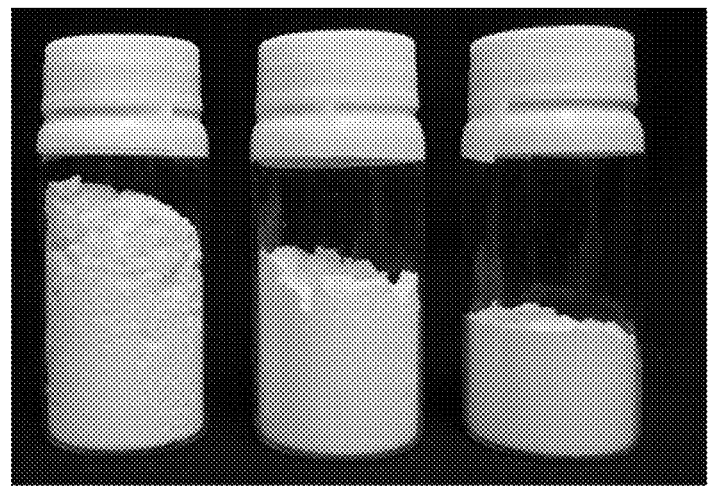
FIG. 1 is a view illustrating powder compositions obtained in Examples 1 to 3.

A "powderizing agent for a liquid component" of the present invention (hereinafter also referred to as a "powderizing agent") contains an oil and/or fat composition described below as an essential component.

<Oil and/or Fat Composition>

When the total triglyceride content is set to 100% by mass, the oil and/or fat composition is an oil and/or fat composition which contains: 65 to 99% by mass of one or more types of XXX-type triglycerides having fatty acid residues X, each with x carbon atoms, at positions 1 to 3; and 35 to 1% by mass of one or more types of X2Y-type triglycerides each having a fatty acid residue Y with y carbon atoms in place of one of the fatty acid residues X of the XXX-type triglyceride, in which x, the number of carbon atoms, is an integer selected from 8 to 20, and y, the number of carbon atoms, is each independently an integer selected from x+2 to x+12 and satisfies y≤22.

Hereinafter, a description is provided in detail for the XXX-type triglyceride and the X2Y-type triglyceride.

<XXX-Type Triglyceride>

The oil and/or fat composition used in the present invention contains a single type or more types, preferably a single type (one type) of XXX-type triglyceride the content of which, when the total triglyceride content is set to 100% by mass, is 65 to 99% by mass.

The XXX-type triglyceride is a triglyceride having fatty acid residues X, each with x carbon atoms, at positions 1 to 3, and the fatty acid residues X are identical to each other. Here, x, the number of carbon atoms, is an integer selected from 8 to 20, preferably an integer selected from 10 to 18, more preferably an integer selected from 10 to 16, and further preferably an integer selected from 10 to 12.

The fatty acid residue X may be a saturated or unsaturated fatty acid residue. Specifically, the fatty acid residue X includes, but is not limited to, residues of caprylic acid, capric acid, lauric acid, myristic acid, palmitic acid, stearic acid, and arachidic acid, for example. The fatty acid is more preferably capric acid, lauric acid, myristic acid, palmitic acid, and stearic acid, further preferably capric acid, lauric acid, myristic acid, and palmitic acid, and especially preferably capric acid and lauric acid.

When the total triglyceride content in the oil and/or fat composition is set to 100% by mass, the XXX-type triglyceride is contained at 65 to 99% by mass. The content of XXX-type triglyceride is preferably 75 to 99% by mass, more preferably 80 to 99% by mass, further preferably 83 to 98% by mass, particularly preferably 85 to 98% by mass, and especially preferably 90 to 98% by mass.

<X2Y-Type Triglyceride>

The oil and/or fat composition used in the present invention contains one or more types of X2Y-type triglycerides each having a fatty acid residue Y with y carbon atoms in place of one of the fatty acid residues X of the XXX-type triglyceride. Here, the fatty acid residues X contained in one X2Y-type triglyceride are identical to each other and also identical to the fatty acid residues X of the XXX-type triglyceride. The number of carbon atoms y of the fatty acid residue Y contained in one X2Y-type triglyceride is an integer selected based on the conditions that x+2 to x+12 and y≤22. The number of carbon atoms y is an integer selected based on the conditions of preferably satisfying y=x+2 to x+10 and more preferably satisfying y=x+4 to x+8. In addition, the upper limit value of y, the number of carbon atoms, is preferably y≤20 and more preferably y≤18. The oil and/or fat composition used in the present invention may contain multiple, for example two types to five types, preferably 3 or 4 types of X2Y-type triglycerides. In that case, the definition of each of the X2Y-type triglycerides is as described above. The numbers of carbon atoms y of the fatty acid residues Y of the X2Y-type triglycerides are each independently selected from the above-described range for the X2Y-type triglyceride. For example, although x has a common value of x=10, production of the oil and/or fat composition of the present invention by transesterification of tricaprin and extremely hardened palm kernel stearin oil involves four types of X2Y-type triglycerides in which y has the values of y=12, 14, 16, and 18.

The fatty acid residue Y may be a saturated or unsaturated fatty acid residue. Specifically, the fatty acid residue Y includes, but is not limited to, residues of lauric acid, myristic acid, palmitic acid, stearic acid, arachidic acid, and behenic acid, for example. The fatty acid is more preferably myristic acid, palmitic acid, stearic acid, arachidic acid, and behenic acid and further preferably myristic acid, palmitic acid, and stearic acid. The fatty acid residue Y of this X2Y-type triglyceride may be positioned at any of the positions 1 to 3.

When the total triglyceride content in the oil and/or fat composition is set to 100% by mass, the X2Y-type triglyceride is contained at 35 to 1% by mass. The content of X2Y-type triglyceride is, for example, 25 to 1% by mass, preferably 20 to 1% by mass, more preferably 17 to 1% by mass, further preferably 15 to 2% by mass, and especially preferably 10 to 2% by mass. If the oil and/or fat composition used in the present invention contains multiple X2Y-type triglycerides, the amount of the X2Y-type triglycerides is the total amount of the X2Y-type triglycerides contained.

<Other Triglycerides>

The oil and/or fat composition may contain other triglycerides other than the XXX-type triglyceride and the X2Y-type triglyceride described above as long as the effects of the present invention are not impaired. The other triglyceride may be multiple types of triglycerides or any of synthetic oils and/or fats and natural oils and/or fats. The synthetic oils and/or fats include glyceryl tricaprylate, glyceryl tricaprate, glyceryl trilaurate, and the like. The natural oils and/or fats include, for example, cocoa butter, sunflower oil, rapeseed oil, soybean oil, and cottonseed oil. Note that if present in the liquid form, these synthetic oils and/or fats may be used as a liquid component to be powderized. When the total triglyceride content in the oil and/or fat composition used in the present invention is set to 100% by mass, no problem arises if the other triglycerides are contained at 1% by mass or more, for example about 5 to 30% by mass. The content of the other triglycerides is, for example, 0 to 30% by mass, preferably 0 to 18% by mass, more preferably 0 to 15% by mass, and further preferably 0 to 8% by mass.

<Method of Producing Oil and/or Fat Composition>

The oil and/or fat composition used in the present invention can be a liquid form oil and/or fat composition in the molten state or a powdered oil and/or fat composition in the solid state. First, a description is provided below for a method of producing the liquid form oil and/or fat composition.

Production is possible by a method including the following steps:

(a) a step of preparing an oil and/or fat composition which contains, when the total triglyceride content is set to 100% by mass, 65 to 99% by mass of XXX-type triglyceride having fatty acid residues X, each with x carbon atoms, at positions 1 to 3 and 35 to 1% by mass of X2Y-type triglyceride having a fatty acid residue Y with y carbon atoms in place of one of the fatty acid residues X of the XXX-type triglyceride, in which x, the number of carbon atoms, is an integer selected from 8 to 20, and y, the number of carbon atoms, is each independently an integer selected from x+2 to x+12 and satisfies y≤22; and (b) a step of obtaining the oil and/or fat composition in the molten state by heating the oil and/or fat composition to melt the triglyceride contained in the oil and/or fat composition.

Hereinafter, a description is provided for steps (a) and (b) described above.

(a) Step I of Preparing Oil and/or Fat Composition

The oil and/or fat composition prepared in step (a) contains the XXX-type triglyceride (one or more types) and X2Y-type triglyceride (one or more types) as described above at the above-described mass percentages. Specifically, for example, the oil and/or fat composition can be obtained through the step of: separately obtaining the XXX-type triglyceride (one or more types) having fatty acid residues X, each with x carbon atoms, at positions 1 to 3 and the YYY-type triglyceride (one or more types) having fatty acid residues Y, each with y carbon atoms, at positions 1 to 3; obtaining a reaction substrate by mixture at a mass ratio of the XXX-type triglyceride/YYY-type triglyceride being 90/10 to 99/1 (here, x, the number of carbon atoms, is an integer selected from 8 to 20, and y, the number of carbon atoms, is an integer selected from x+2 to x+12 and satisfies y≤22); heating the reaction substrate; and performing a transesterification reaction in the presence of a catalyst.

<Reaction Substrate>

First, the XXX-type triglyceride (one or more types) and the YYY-type triglyceride (one or more types) are mixed to obtain a reaction substrate. Here, the details of the XXX-type triglyceride are as described above.

The YYY-type triglyceride is a triglyceride having fatty acid residues Y, each with y carbon atoms, at positions 1 to 3. Here, y, the number of carbon atoms, and the fatty acid residue Y are as described above.

The XXX-type triglyceride and the YYY-type triglyceride can also be obtained by direct synthesis using a fatty acid or a fatty acid derivative and glycerin. Taking the XXX-type triglyceride as an example, a method of directly synthesizing the XXX-type triglyceride includes (i) a method of directly esterifying a fatty acid having X carbon atoms and glycerin (direct ester synthesis), (ii) a method of reacting glycerin with a fatty acid alkyl (for example, a fatty acid methyl and a fatty acid ethyl), in which a carboxyl group of a fatty acid X having x carbon atoms is bonded to an alkoxyl group, under a condition of a basic or acidic catalyst (transesterification synthesis using a fatty acid alkyl), and (iii) a method of reacting glycerin with a fatty acid halide (for example, a fatty acid chloride and a fatty acid bromide), in which a hydroxyl group of a carboxyl group of the fatty acid X having x carbon atoms is substituted with a halogen, in the presence of a basic catalyst (acid halide synthesis).

Although the XXX-type triglyceride and the YYY-type triglyceride can be produced by any of the methods (i) to (iii) described above, (i) the direct ester synthesis or (ii) the transesterification synthesis using a fatty acid alkyl is preferable and (i) the direct ester synthesis is more preferable from the viewpoint of easiness of production.

In order to produce the XXX-type triglyceride or the YYY-type triglyceride by (i) the direct ester synthesis, the fatty acid X or the fatty acid Y is used preferably in 3 to 5 moles and is used more preferably in 3 to 4 moles relative to 1 mole of glycerin from the viewpoint of production efficiency.

The reaction temperature of the XXX-type triglyceride or the YYY-type triglyceride in (i) the direct ester synthesis may be a temperature which makes it possible to remove generation water generated by the esterification reaction to the outside of the system, and is preferably 120° C. to 300° C., more preferably 150° C. to 270° C., and further preferably 180° C. to 250° C., for example. If the reaction is performed at 180 to 250° C., it is possible to particularly efficiently produce the XXX-type triglyceride or the YYY-type triglyceride.

In (i) the direct ester synthesis of the XXX-type triglyceride or the YYY-type triglyceride, a catalyst which promotes esterification reaction may be used. The catalyst includes an acidic catalyst, an alkaline earth metal alkoxide, and the like. The amount of catalyst used is preferably about 0.001 to 1% by mass relative to the total mass of the reaction raw materials.

In (i) the direct ester synthesis of the XXX-type triglyceride or the YYY-type triglyceride, after the reaction, it is possible to remove the catalyst and the unreacted raw materials by performing known purification treatment such as water washing, alkali deacidification and/or pressure reducing deacidification, and adsorption treatment. Moreover, by implementing bleaching and deodorization treatment, it is possible to further purify the obtained reaction product.

These XXX-type triglyceride and YYY-type triglyceride are mixed at a mass ratio of the XXX-type triglyceride/YYY-type triglyceride being 90/10 to 99/1, preferably 93/7 to 99/1, and more preferably 95/5 to 99/1. Particularly, if the fatty acid residue X has 10 carbon atoms and the fatty acid residue Y has 14 to 18 carbon atoms, the mass ratio of the XXX-type triglyceride/YYY-type triglyceride is preferably 95/5 to 99/1. In addition, if the fatty acid residue X has 12 carbon atoms and the fatty acid residue Y has 16 to 18 carbon atoms, the mass ratio of the XXX-type triglyceride/YYY-type triglyceride is preferably 95/5 to 99/1.

<Other Triglycerides>

As the triglyceride being a raw material of the reaction substrate, various types of triglycerides may be contained including the XXX-type triglyceride and the YYY-type triglyceride described above as long as the effects of the present invention are not impaired. The other triglycerides include, for example, a X2Y-type triglyceride having the fatty acid residue Y in place of one of the fatty acid residues X of the XXX-type triglyceride and a XY2-type triglyceride having the fatty acid residues Y in place of two of the fatty acid residues X of the XXX-type triglyceride.

When the total mass of the XXX-type triglyceride and the YYY-type triglyceride is set to 100% by mass, the amount of the other triglycerides is, for example, 0 to 15% by mass, preferably 0 to 7% by mass, and more preferably 0 to 4% by mass.

In addition, instead of the XXX-type triglyceride and the YYY-type triglyceride, a triglyceride composition of natural origin may be used. The triglyceride composition of natural origin includes, for example, palm kernel oil, palm kernel olein, palm kernel stearin, rapeseed oil, coconut oil, soybean oil, sunflower oil, safflower oil, and palm stearin. Moreover, these triglyceride compositions of natural origin may be a hydrogenated oil, a partially hydrogenated oil, and an extremely hardened oil which are modified by e.g. hydrogenation.

Although the amount of the triglyceride compositions of natural origin depends on the necessary amount of the XXX-type triglyceride or the YYY-type triglyceride contained in these triglyceride compositions of natural origin, it is appropriate that, for example if each of the X's of the XXX-type triglyceride is capric acid and extremely hardened palm kernel stearin oil is used as the origin of the YYY-type triglyceride, a triglyceride which has the residues Y at positions 1 to 3 contained in the extremely hardened palm kernel stearin oil is contained in an amount necessary as the YYY-type triglyceride described above, in other words in other words in such an amount that satisfies the mass ratio of the XXX-type triglyceride/YYY-type triglyceride being 90/10 to 99/1, preferably 93/7 to 99/1, and more preferably 95/5 to 98/2.

<Other Components>

In addition to the triglycerides described above, the raw materials constituting the reaction substrate may optionally contain other components such as a partial glyceride, an antioxidant, an emulsifier, and a solvent such as water. The amount of the other components can be any amount as long as the effects of the present invention are not impaired and is, for example, 0 to 5% by mass, preferably 0 to 2% by mass, and more preferably 0 to 1% by mass when the mass of the obtained reaction substrate is set to 100% by mass.

Although any known mixing method may be used as long as a homogeneous reaction substrate is obtained, the mixing can be performed with, for example, a paddle mixer, an agi homo mixer, a disper mixer, and the like.

Regarding the mixing, the mixing may be performed under heating as necessary. The heating is preferably the same as the heating temperature in step (b) to be described later, and is performed at, for example, 50 to 120° C., preferably 60 to 100° C., more preferably 70 to 90° C., and further preferably 80° C. Note that if an enzyme is added as a catalyst, water is present preferably in an amount as little as possible before the addition of an enzyme. It is appropriate that the amount of water before the addition of an enzyme is, for example, 10% by mass or less, preferably 0.001 to 5% by mass, more preferably 0.01 to 3% by mass, and further preferably 0.01 to 2% by mass relative to the total mass of the raw materials. This mixing may continue for 5 to 60 minutes, preferably 10 to 50 minutes, and more preferably 20 to 40 minutes, for example.

<Transesterification Reaction>

A transesterification reaction product (an oil and/or fat composition containing the XXX-type triglyceride and the X2Y-type triglyceride) is obtained by heating the reaction substrate (a mixture containing the XXX-type triglyceride and the YYY-type triglyceride) described above, followed by transesterification reaction in the presence of a catalyst.

Regarding the transesterification reaction, it is possible to use a usually used transesterification reaction without particular limitation.

Here, the heating is performed at, for example, 50 to 120° C., preferably 60 to 100° C., more preferably 70 to 90° C., and further preferably 80° C.

As the catalyst, it is possible to use an enzyme, an alkali metal alkoxide, an alkaline earth metal alkoxide, and the like. As the enzyme, it is possible to use an immobilized enzyme and a powder enzyme, but the powder enzyme is preferable in terms of enzyme activity and handling easiness.

The powder enzyme is one obtained by drying an enzyme-containing water-based liquid and powderizing the enzyme-containing water-based liquid by a method such as spray drying, freeze drying, and drying after solvent precipitation, and examples thereof include, but are not limited to, a lipase originating from Alcaligenes sp. (Meito Sangyo Co., Ltd., trade name of Lipase QLM).

As the immobilized enzyme, it is possible to use one obtained by immobilizing an enzyme to a support such as silica, Celite, diatomaceous earth, perlite, polyvinyl alcohol, an anion-exchange resin, a phenol absorbing resin, a hydrophobic support, a cation-exchange resin, and a chelating resin.

Regarding the alkali metal alkoxides and the alkaline earth metal alkoxides usable as a catalyst, the alkali metals preferably usable include lithium, sodium, potassium, and the like. The alkaline earth metals preferably usable include magnesium and calcium. The alkoxides include a methoxide, an ethoxide, a propoxide, n-butoxide, t-butoxide, and the like, and are preferably a methoxide and an ethoxide. Preferable alkali metal alkoxides and alkaline earth metal alkoxides include sodium methoxide, sodium ethoxide, magnesium methoxide, magnesium ethoxide, and the like, and are more preferably sodium methoxide.

These catalysts may be used singly or in combination of two or more types, but it is preferable that an enzyme-based catalyst and an alkoxide-based catalyst are not used at the same time.

The amount of catalyst may be such an amount that transesterification reaction sufficiently proceeds, and the amount added is, for example, 0.01 to 20% by mass, preferably 0.05 to 10% by mass, more preferably 0.1 to 5% by mass, and further preferably 0.2 to 1% by mass relative to the total mass of the triglycerides being raw materials. An optional auxiliary catalyst may be used in addition to the catalysts described above.

The transesterification reaction is performed together with optional stirring under, for example, normal pressure or under reduced pressure and at the heating temperature described above for 0.5 to 50 hours, preferably 1 to 40 hours, more preferably 5 to 30 hours, and further preferably 10 to 20 hours, for example. In addition, although the predetermined amount of catalyst may be introduced, for example, at a time in this reaction step, the predetermined amount of catalyst may be introduced separately in 2 to 30 times, preferably 3 to 20 times, and more preferably 5 to 15 times. The timing of introducing the catalyst may be immediately after step (a) described above or at intervals of 1 to 2 hours after the first introduction of the catalyst.

(a) Step II of Preparing Oil and/or Fat Composition

The method of producing the oil and/or fat composition prepared in step (a) further includes a method of synthesizing simultaneously and directly the XXX-type triglyceride and the X2Y-type triglyceride as described later. To be more specific, in order to obtain the XXX-type triglyceride and the X2Y-type triglyceride, preparation step II does not separately synthesize the XXX-type triglyceride and the YYY-type triglyceride for transesterification but introduces the raw materials (a fatty acid or a fatty acid derivative and glycerin) for producing both triglycerides into, for example, a single reaction vessel for simultaneous and direct synthesis. The production method thereof includes any of the following methods.

The method includes (iv) a method of directly esterifying glycerin with a fatty acid X having X carbon atoms and a fatty acid Y having y carbon chains (direct ester synthesis), (v) a method of reacting glycerin with a fatty acid alkyl (for example, a fatty acid methyl and a fatty acid ethyl), in which a carboxyl group of each of the fatty acid X having x carbon atoms and the fatty acid Y having y carbon chains is bonded to an alkoxyl group, under a condition of a basic or acidic catalyst (transesterification synthesis using a fatty acid alkyl), and (vi) a method of reacting glycerin with a fatty acid halide (for example, a fatty acid chloride and a fatty acid bromide), in which a hydroxyl group of a carboxyl group of each of the fatty acid X having x carbon atoms and the fatty acid Y having y carbon chains is substituted with a halogen, in the presence of a basic catalyst (acid halide synthesis).

Although the oil and/or fat composition used in the present invention can be produced by any of the methods described above, (iv) the direct ester synthesis or (v) the transesterification synthesis using a fatty acid alkyl is preferable and (iv) the direct ester synthesis is more preferable from the viewpoint of easiness of production.

In (iv) the direct ester synthesis of the oil and/or fat composition used in the present invention, the production method is not limited as long as the XXX-type triglyceride and the X2Y-type triglyceride in all the triglycerides are each within a range of desired mass percentage. For the purpose of reliably generating desired triglycerides in the system, it is preferable to perform a two-stage reaction. To be more specific, the method preferably includes a first stage of reacting glycerin with the fatty acid X having x carbon atoms, which contains the fatty acid Y having y carbon atoms, and a second stage of adding the fatty acid X having x carbon chains for reaction to produce an oil and/or fat composition containing a predetermined amount of the XXX-type triglyceride and the X2Y-type triglyceride.

When performing the two-stage reaction, in the reaction at the first stage, the total molar amount of the fatty acid X and the fatty acid Y, adjusted within such a range that the X2Y-type triglyceride in all glycerides is at a desired mass percentage, is preferably 0.5 to 2.8 in molar amount, more preferably 0.8 to 2.57 molar amount, and most preferably 1.1 to 2.2 molar amount relative to 1 mole of glycerin. This reliably allows esterification of all of the fatty acid Y with glycerin and makes it possible to more reliably generate the X2Y-type triglyceride finally in the system.

The reaction temperature in the direct ester synthesis of the oil and/or fat composition used in the present invention may be a temperature which makes it possible to remove generation water generated by the esterification reaction to the outside of the system, and is preferably 120° C. to 300° C., more preferably 150° C. to 270° C., and further preferably 180° C. to 250° C. If the reaction takes place particularly at 180 to 250° C., it is possible to efficiently produce the X2Y-type triglyceride.

In the direct ester synthesis of the oil and/or fat composition used in the present invention, a catalyst which promotes esterification reaction may be used. The catalyst includes an acidic catalyst, an alkaline earth metal alkoxide, and the like. The amount of catalyst used is preferably about 0.001 to 1% by mass relative to the total mass of the reaction raw materials.

In (iv) the direct ester synthesis of the oil and/or fat composition used in the present invention, after the reaction, it is possible to remove the catalyst and the unreacted raw materials by performing known purification treatment such as water washing, alkali deacidification and/or pressure reducing deacidification, and adsorption treatment. Moreover, by implementing bleaching and deodorization treatment, it is possible to further purify the obtained reaction product.

(a) Step III of Preparing Oil and/or Fat Composition

The oil and/or fat composition may be obtained as follows. An oil and/or fat composition containing the XXX-type triglyceride outside the range of 65 to 99% by mass and/or the X2Y-type triglyceride outside the range of 35 to 1% by mass is further prepared, followed by further addition of the XXX-type triglyceride or the X2Y-type triglyceride to obtain an oil and/or fat composition containing 65 to 99% by mass of the XXX-type triglyceride and 35 to 1% by mass of the X2Y-type triglyceride (preparation of an oil and/or fat composition by dilution). For example, an oil and/or fat composition may be obtained as follows. An oil and/or fat composition containing 50 to 70% by mass of the XXX-type triglyceride and 50 to 30% by mass of the X2Y-type triglyceride is obtained, followed by addition of a desired amount of the XXX-type triglyceride to obtain an oil and/or fat composition containing 65 to 99% by mass of the XXX-type triglyceride and 35 to 1% by mass of the X2Y-type triglyceride.

Moreover, preparation step III described above includes once preparing an oil and/or fat composition containing the XXX-type triglyceride within the range of 65 to 99% by mass and/or the X2Y-type triglyceride within the range of 35 to 1% by mass by preparation step I or II described above, followed by further addition of the XXX-type triglyceride or the X2Y-type triglyceride to adjust the mass percentage of each of the XXX-type triglyceride and the X2Y-type triglyceride to a more preferable range (preparation of an even more preferable oil and/or fat composition by dilution).

(b) Step of Obtaining Above-Described Oil and/or Fat Composition in Molten State The oil and/or fat composition obtained in step (a) described above is then cooled without heating if in the molten state at the time of preparation. However, if not in the molten state when obtained, the oil and/or fat composition is heated to melt the triglycerides contained in the oil and/or fat composition. As a result, the oil and/or fat composition in the molten state is obtained.

Here, it is appropriate that the heating of the oil and/or fat composition is performed at a temperature equal to or more than the melting points of the triglycerides contained in the oil and/or fat composition described above, particularly at a temperature which makes it possible to melt the XXX-type triglyceride and the X2Y-type triglyceride, for example 70 to 200° C., preferably 75 to 150° C., and more preferably 80 to 100° C. In addition, it is appropriate that the heating is continued for 0.5 to 3 hours, preferably 0.5 to 2 hours, and more preferably 0.5 to 1 hour, for example.

As described above, it is possible to produce a liquid form oil and/or fat composition in the molten state of the present invention (an embodiment of the powderizing agent in the present invention).

Next, a description is provided for a method of producing a powdered oil and/or fat composition in the solid state of the present invention (another embodiment of the powderizing agent in the present invention). A powdered oil and/or fat composition (hereinafter also referred to as a "powder oil and/or fat composition") is produced, by step (d) described below, by further cooling the oil and/or fat composition obtained by step (a) and step (b) described above. Note that it is necessary to perform cooling at the cooling temperature described later in order to produce the powder oil and/or fat composition.

(d) Step of Obtaining Powder Oil and/or Fat Composition by Cooling Oil and/or Fat Composition in Molten State The oil and/or fat composition in the molten state is further cooled to form a powder oil and/or fat composition.

Here, "cool the oil and/or fat composition in the molten state" means to maintain the oil and/or fat composition in the molten state at a temperature lower than the melting point of the oil and/or fat composition. The "temperature lower than the melting point of the oil and/or fat composition" is, for example, a temperature lower than the melting point by 1 to 30° C., preferably a temperature lower than the melting point by 1 to 20° C., and more preferably a temperature lower than the melting point by 1 to 15° C. If x (the number of carbon atoms of the fatty acid residue X) is 8 to 10, for example, the cooling of the oil and/or fat composition in the molten state is performed such that the final temperature reaches a temperature of preferably 10 to 30° C., more preferably 15 to 25° C., and further preferably 18 to 22° C. For example, the final temperature in the cooling is preferably 30 to 40° C., more preferably 32 to 38° C., further preferably 33 to 37° C. if x is 11 or 12, preferably 40 to 50° C., more preferably 42 to 48° C., further preferably 44 to 47° C. if x is 13 or 14, preferably 50 to 60° C., more preferably 52 to 58° C., further preferably 54 to 57° C. if x is 15 or 16, preferably 60 to 70° C., more preferably 62 to 68° C., further preferably 64 to 67° C. if x is 17 or 18, and preferably 70 to 80° C., more preferably 72 to 78° C., further preferably 74 to 77° C. if x is 19 or 20. It is appropriate to allow the oil and/or fat composition to stand at the final temperature described above for preferably 2 hours (120 minutes) or more, more preferably 4 hours (240 minutes) or more, and further preferably 6 hours to 2 days, for example. If x is 8 to 12 in particular, the stand time could be about 2 to 6 days.

(c) Step of Promoting Generation of Powder

As an optional step (c) for promoting the generation of powder between step (a) or (b) and (d) described above, one may further perform the treatment of a seeding process (c1), a tempering process (c2), and/or (c3) a pre-cooling process on the oil and/or fat composition in the molten state to be used in step (d). These optional steps (c1) to (c3) may be performed singly or in combination of two or more steps. Here, between step (a) or (b) and step (d) has a meaning which includes within step (a) or (b) and after step (a) or (b), and before step (d) and within step (d). The seeding process (c1) and the tempering process (c2) are each a method of promoting the generation of powder in the production of the powder oil and/or fat composition of the present invention, which treats the oil and/or fat composition in the molten state before cooling to the final temperature in order to more reliably powderize the oil and/or fat composition in the molten state.

Here, the seeding process is a method of promoting powderization by adding a small amount of a component being a core (seed) of powder in the cooling of the oil and/or fat composition in the molten state. To be more specific, for example, together with the oil and/or fat composition in the molten state obtained in step (b) an oil and/or fat powder which contains a XXX-type triglyceride having carbon atoms equal to those of the XXX-type triglyceride in the oil and/or fat composition at preferably 80% by mass or more and more preferably 90% by mass or more, is prepared as a core (seed) component. The method promotes the powderization of the oil and/or fat composition by adding this oil and/or fat powder being the core at 0.1 to 1 part by mass and preferably 0.2 to 0.8 parts by relative to 100 parts by mass of the oil and/or fat composition in the molten state when, in the cooling of the oil and/or fat composition in the molten state, the temperature of the oil and/or fat composition reaches a temperature of the final cooling temperature±0 to +10° C. and preferably +5 to +10° C., for example.

The tempering process is a method of promoting the powderization of the oil and/or fat composition by, before allowing the oil and/or fat composition to stand at the final cooling temperature in the cooling of the oil and/or fat composition in the molten state, once performing cooling at a temperature lower than the cooling temperature of step (d), for example a temperature lower by 5 to 20° C., a temperature lower by preferably 7 to 15° C., and a temperature lower by more preferably about 10° C. for preferably 10 to 120 minutes and more preferably about 30 to 90 minutes.

(c3) The pre-cooling process is a method of, before cooling in step (d), once pre-cooling the oil and/or fat composition in the molten state obtained in step (a) or (b) described above at a temperature lower than the temperature of the molten state of step (a) or (b) and at a temperature higher than the cooling temperature of step (d). The temperature higher than the cooling temperature of step (d) can be, for example, a temperature higher by 2 to 40° C., a temperature higher by preferably 3 to 30° C., a temperature higher by more preferably 4 to 30° C., and a temperature higher by further preferably about 5 to 10° C. than the cooling temperature of step (d). The lower the temperature for pre-cooling, the shorter the main cooling time at the cooling temperature of step (d) can be. To sum up, unlike the seeding process and the tempering process, the pre-cooling process is a method which can promote the powderization of the oil and/or fat composition by simply lowering step by step the cooling temperature, and has a great advantage in the case of industrial production.

(e) Step of Obtaining Powder Oil and/or Fat Composition by Pulverizing a Solid.

The above step of obtaining the powder oil and/or fat composition by cooling of step (d) may be, more specifically, performed by step (e) of obtaining the powder oil and/or fat composition by pulverizing a solid obtained by cooling of step (d).

To explain the details, the oil and/or fat composition containing the XXX-type triglyceride and the X2Y-type triglyceride is first melted to obtain the oil and/or fat composition in the molten state, followed by cooling to form a solid having voids with an increased volume larger than the oil and/or fat composition in the molten state. The oil and/or fat composition formed into a solid having voids can easily be pulverized by applying a weak impact thereto. The solid easily collapses into a powder form.

Here, although the means of applying a weak impact is not particularly limited, a method of applying weak vibration (impact) for pulverization (loosening) by, for example, shaking or sieving is preferable because of its simplicity.

As described above, it is possible to produce a powder-form powder oil and/or fat composition in the solid state of the present invention.

<Optional Component in Oil and/or Fat Composition>

It is preferable that the oil and/or fat composition used in the present invention (which has two embodiments of a liquid form and a powder form) is essentially composed only of oil and/or fat. Here, the oil and/or fat is essentially composed only of triglycerides. In addition, "essentially" means that the components other than the oil and/or fat contained in the oil and/or fat composition or the components other than the triglycerides contained in the oil and/or fat are, for example, 0 to 15% by mass, preferably 0 to 10% by mass, and more preferably 0 to 5% by mass when the oil and/or fat composition or the oil and/or fat is set to 100% by mass.

<Powderizing Agent>

The powderizing agent of the present invention contains the above-described oil and/or fat composition (which has two embodiments of a liquid form and a powder form) as an essential component.

The powdered oil and/or fat composition used as the powderizing agent of the present invention is preferably a powder body having an average particle diameter of 10 to 1000 μm, more preferably a powder body having an average particle diameter of 20 to 400 μm, and further preferably a powder body having an average particle diameter of 50 to 300 μm. If a powder body having the average particle diameter described above is used, it is possible to obtain a smooth powder composition having a uniform distribution of the liquid component and the powderizing agent. Note that the average particle diameter mentioned here is a value measured by laser diffraction scattering method (ISO 133201 and ISO 9276-1).

In addition, a powder body having the average particle diameter described above can be produced by using known pulverization means, for example spraying or a pulverizer, which is generally used for production of oils and/or fats.

It is preferable that the powderizing agent of the present invention is composed only of the oil and/or fat composition.

Note that the powderizing agent of the present invention may contain an optional component in addition to the oil and/or fat composition described above as long as the functions as the powderizing agent are not impaired. The optional component mentioned here refers to a component other than the liquid component (powderization target) to be described later. The optional component includes an emulsifier, skim milk powder, whole milk powder, cocoa powder, sugar, dextrin, and the like.

The amount of the optional component blended is, for example, 0 to 70% by mass, preferably 0 to 65% by mass, and more preferably 0 to 30% by mass when the total mass of the powderizing agent is set to 100% by mass.

Preferably, 90% by mass or more of the optional component is a powder body having an average particle diameter of 1000 μm or less and more preferably a powder body having an average particle diameter of 500 μm or less from the viewpoint that it is possible to obtain a smooth powder composition having a uniform distribution of the liquid component and the powderizing agent. Note that the average particle diameter mentioned here is a value measured by laser diffraction scattering method (ISO 133201 and ISO 9276-1).

Next, a description is provided for a method of powderizing the liquid component by using the powderizing agent of the present invention (in other words, a method of producing a powder composition by powderizing the liquid component).

<Liquid Component>

The liquid component refers to a liquid which contains the functional materials contained in the product to be described later.

In addition, the liquid component refers to a component which is a liquid at normal temperature (20° C.).

Regarding the functional materials, it is possible to use ones capable of adding a certain function to the product without particular limitation.

In addition, the functional materials may be a substance which adds a primary function of the product (for example, active components in medicinal drugs or functional foods) or a substance which adds a secondary function of the product (for example, dyes and flavors in food).

The functional material may be used singly or in appropriate combination of two or more types.

The functional material can be divided into hydrophobic substances and hydrophilic substances.

<Hydrophobic Substance>

Regarding the hydrophobic substances, it is possible to use ones blended in the product described later as functional materials without particular limitation. Specific examples include a flavor, a dye, a vitamin, a lipid, a protein (hydrophobic peptide), and the like. Among these, the present invention is preferably applicable to a flavor, a dye, a vitamin, and lecithin.

Regarding the flavor, it is possible to use, for example, ones blended in foods and/or beverages, cosmetics, quasi drugs, pharmaceutical drugs, and the like without particular limitation. Specific examples include menthol, cocoas (powder, extract, and the like), esters (for example, isoamyl acetate, linalyl acetate, isoamyl propionate, linalyl butyrate, and the like), natural essential oils (examples of plant essential oil are vanilla extract, spearmint, peppermint, cassia, jasmine, and the like; examples of animal essential oil are musk, ambergris, civet, castoreum, and the like), aromatic chemicals (for example, anethole, limonene, linalool, eugenol, vanillin, and the like), and oily seasonings (roasted shrimp oil, onion oil, and the like), and more specifically include limonene, vanillin, roasted shrimp oil, onion oil, and the like.

Regarding the dye, it is possible to use, for example, ones blended in foods and/or beverages, cosmetics, quasi drugs, pharmaceutical drugs, and the like without particular limitation. Specific examples include an orange dye, a yellow dye, a magenta dye, a cyan dye, and the like.

Regarding the vitamin, it is possible to use, for example, ones blended in foods and/or beverages, cosmetics, quasi drugs, pharmaceutical drugs, and the like without particular limitation. Specific examples include vitamin E, vitamin A, vitamin D, vitamin K, and the like.

Regarding the lipid, it is possible to use, for example, ones blended in foods and/or beverages, cosmetics, quasi drugs, pharmaceutical drugs, and the like without particular limitation. Specific examples include a triglyceride, a fatty acid, a phospholipid (for example, lecithin, lysolecithin, phosphatidic acid, lysophosphatidic acid, and the like), triethylhexanoin, and the like.

The protein includes a hydrophobic peptide, and the peptide is a series of 3 or more amino acids. Hydrophobicity means a low solubility to water, and hydrophobicity is here defined to be a solubility of less than 1 μg per 1 ml of water.

The hydrophobic substance may be used singly or in appropriate combination of two or more types for use as a mixture.

The liquid component may be a solution of the hydrophobic substances. Regarding the solvent constituting the solution, it is possible to use ones capable of dissolving the hydrophobic substances without particular limitation. Specific examples include a liquid oil, an alcohol, an organic solvent, and the like. Regarding the solution of the hydrophobic substances, it is preferable that the solution itself is hydrophobic.

Regarding the liquid oil, it is possible to use, for example, ones blended in foods and/or beverages, cosmetics, quasi drugs, pharmaceutical drugs, and the like without particular limitation. Specific examples include edible oil and/or fats such as rapeseed oil, olive oil, rice bran oil, sesame oil, cottonseed oil, peanut oil, corn oil, soybean oil, sunflower oil, safflower oil, grape seed oil, macadamia nut oil, hazelnut oil, pumpkin seed oil, walnut oil, tea seed oil, tea oil, MCT oil, and MLCT oil (note that the XXX-type triglyceride and the X2Y-type triglyceride described above are excluded).

Regarding the alcohol, it is possible to use, for example, ones blended in foods and/or beverages, cosmetics, quasi drugs, pharmaceutical drugs, and the like without particular limitation. Specific examples include, for example, lower alcohols such as methyl alcohol, ethyl alcohol, n-propyl alcohol, isopropyl alcohol, or butyl alcohol.

Regarding the organic solvent, it is possible to use, for example, ones blended in foods and/or beverages, cosmetics, quasi drugs, pharmaceutical drugs, and the like without particular limitation. Specific examples include ethyl acetate, butyl acetate, diethyl ether, methyl ether, methyl isobutyl ketone, hexane, acetone, chloroform, or the like.

The solvent may be used singly or in appropriate combination of two or more types for use as a mixture.

Although no particular limitation is imposed, the content of the hydrophobic substances in the solution is, for example, 1 to 99% by mass, preferably 5 to 80% by mass, and further preferably 10 to 60% by mass relative to the total mass of the solution.

The liquid component may be an emulsion of the hydrophobic substances. Regarding the dispersion medium constituting the emulsion, it is possible to use ones capable of dispersing the hydrophobic substances without particular limitation. Specific examples include water, glycerin, a sugar alcohol, a liquid oil, and the like, preferably water, glycerin, and a liquid oil, and more preferably water and glycerin.

The dispersion medium may be used singly or inappropriate combination of two or more types.

The emulsion may contain an emulsifier. Regarding the emulsifier, it is possible to use ones capable of dispersing the hydrophobic substances without particular limitation. Specific examples include glycerin fatty acid ester, propylene glycol fatty acid ester, sucrose fatty acid ester, polyglycerin fatty acid ester, sorbitan fatty acid ester, a fatty acid salt, alkyl sulfuric acid ester, an alkyl amine salt, a quaternary ammonium salt, alkyl betaine, lecithin, Quillaia extract, gum arabic, gum tragacanth, guar gum, karaya gum, xanthan gum, pectin, pullulan, cyclodextrin, alginic acid and salts thereof, carrageenan, gelatin, casein, starch, derivatives of starch, and the like, preferably glycerin fatty acid ester, propylene glycol fatty acid ester, sucrose fatty acid ester, polyglycerin fatty acid ester, lecithin, and sorbitan fatty acid ester, and more preferably glycerin fatty acid ester, sucrose fatty acid ester, polyglycerin fatty acid ester, and lecithin.

The emulsifier may be used singly or in appropriate combination of two or more types.

Although no particular limitation is imposed, the content of the hydrophobic substances in the emulsion is, for example, 1 to 99% by mass, preferably 5 to 80% by mass, and further preferably 10 to 60% by mass relative to the total mass of the solution.

Note that the liquid component may be the molten hydrophobic substances themselves (a melt). In this case, the liquid component is made up only of the hydrophobic substances. The hydrophobic substances usable as a melt include, for example, vitamin E, limonene, vanillin, and the like.

<Hydrophilic Substance>

Regarding the hydrophilic substances, it is possible to use ones blended in the product described later as functional materials without particular limitation. Specific examples include a flavor, a dye, a vitamin, an available carbohydrate, a protein (hydrophilic peptide), a nucleic acid, and the like. Among these, the present invention is preferably applicable to a flavor, a dye, and a vitamin.

Regarding the flavor, it is possible to use, for example, ones blended in foods and/or beverages, cosmetics, quasi drugs, pharmaceutical drugs, and the like without particular limitation. Specific examples include aqueous flavors (for example, shrimp flavor), natural plant flavors (for example, liquorice, Saint John's bread, prunus salicina extract, peach extract, and the like), acids (for example, malic acid, tartaric acid, citric acid, butyric acid, and the like), and the like.

Regarding the dye, it is possible to use, for example, ones blended in foods and/or beverages, cosmetics, quasi drugs, pharmaceutical drugs, and the like without particular limitation. Specific examples include an azine-based dye, an acridine-based dye, a triphenylmethane-based dye, a xanthene-based dye, a porphyrin-based dye, a cyanine-based dye, a phthalocyanine-based dye, a styryl-based dye, a pyrylium-based dye, an azo-based dye, a quinone-based dye, a tetracycline-based dye, a flavone-based dye, a polyene-based dye, a BODIPY (registered trademark)-based dye, an indigoid-based dye, and the like.

Regarding the vitamin, it is possible to use, for example, ones blended in foods and/or beverages, cosmetics, quasi drugs, pharmaceutical drugs, and the like without particular limitation. Specific examples include vitamins B1, B2, and B6, nicotinic acid, pantothenic acid, vitamin B12, vitamin C, and the like.

Regarding the available carbohydrate, it is possible to use, for example, ones blended in foods and/or beverages, cosmetics, quasi drugs, pharmaceutical drugs, and the like without particular limitation. Specific examples include polysaccharides such as starch, dextrin, α-cyclodextrin, dextran, pullulan, gum arabic, tragacanth, and agar, monosaccharides such as glucose, fructose, and galactose, and oligosaccharides.

The protein includes a hydrophilic peptide, and the peptide is a series of 3 or more amino acids. Hydrophilicity means a high solubility to water, and hydrophilicity is here defined to be a solubility of 1 μg or more per 1 ml of water.

The nucleic acid includes deoxyribonucleic acid (DNA), ribonucleic acid (RNA), DNA-RNA hybrid, an oligonucleotide, a polynucleotide, an aptamer, a peptide nucleic acid (PNA), and the like.

The hydrophilic substances may be used singly or in appropriate combination of two or more types for use as a mixture.

The liquid component may be a solution of the hydrophilic substances. Regarding the solvent constituting the solution, it is possible to use ones capable of dissolving the hydrophilic substances without particular limitation. Specific examples include water, an alcohol, an organic solvent, and the like, preferably water and an alcohol, and more preferably water. Regarding the solution of the hydrophilic substances, it is preferable that the solution itself is hydrophilic.

Regarding the alcohol, it is possible to use, for example, ones blended in foods and/or beverages, cosmetics, quasi drugs, pharmaceutical drugs, and the like without particular limitation. Specific examples include, for example, monovalent lower alcohols such as ethanol, n-propanol, isopropanol, and n-butanol; divalent alcohols such as 1,3-butylene glycol, ethylene glycol, and propylene glycol; polyalkylene glycols such as polyethylene glycol, dipropylene glycol, and polypropylene glycol; and polyvalent alcohols such as glycerin, diglycerin, trimethylolpropane, pentaerythritol, and sorbitol.

Regarding the organic solvent, it is possible to use, for example, ones blended in foods and/or beverages, cosmetics, quasi drugs, pharmaceutical drugs, and the like without particular limitation. Specific examples include glycols, esters, ethers, ketones, and the like. The glycols include, for example, ethylene glycol and propylene glycol. The esters include esters of the alcohols and glycols described above with formic acid, acetic acid, propionic acid, and the like, specifically methyl formate, ethyl formate, butyl formate, methyl acetate, ethyl acetate, butyl acetate, ethyl propionate, and the like. The ethers include alkyl ethers and the like of the alcohols and glycols described above, specifically dimethyl ether, diethyl ether, dibutyl ether, methyl ethyl ether, ethyl butyl ether, ethylene glycol monobutyl ether, ethylene glycol acetate monoethyl ether, propylene glycol monoethyl ether, and the like. The ketones include acetone, diethyl ketone, methyl ethyl ketone, acetophenone, and the like.

The solvent may be used singly or in appropriate combination of two or more types for use as a mixture.

Although no particular limitation is imposed, the content of the hydrophilic substances in the solution is, for example, 1 to 99% by mass, preferably 5 to 80% by mass, and further preferably 10 to 70% by mass relative to the total mass of the solution.

The liquid component may be an emulsion of the hydrophilic substances. Regarding the dispersion medium constituting the emulsion, it is possible to use ones capable of dispersing the hydrophilic substances without particular limitation. Specific examples include water, glycerin, a sugar alcohol, a liquid oil, and the like, preferably water, glycerin, and a liquid oil, and more preferably water and glycerin.

The dispersion medium may be used singly or inappropriate combination of two or more types.

The emulsion may contain an emulsifier. Regarding the emulsifier, it is possible to use ones capable of dispersing the hydrophilic substances without particular limitation. Specific examples include sucrose fatty acid ester, polyglycerin fatty acid ester, organic acid monoglycerin fatty acid ester, lysolecithin, and the like, preferably sucrose fatty acid ester, polyglycerin fatty acid ester, and organic acid monoglycerin fatty acid ester, and more preferably sucrose fatty acid ester and organic acid monoglycerin fatty acid ester.

The emulsifier may be used singly or in appropriate combination of two or more types.

Although no particular limitation is imposed, the content of the hydrophilic substances in the emulsion is, for example, 1 to 99% by mass, preferably 5 to 80% by mass, and further preferably 10 to 60% by mass relative to the total mass of the solution.

Note that the liquid component may be the molten hydrophilic substances themselves (a melt). In this case, the liquid component is made up only of the hydrophilic substances. The hydrophilic substances usable as a melt include, for example, water, a sugar alcohol (for example, erythritol, maltitol, and the like), and the like.

In addition, the liquid component may be ones containing hydrophobic substances and/or hydrophilic substances, for example liquid form food. Specific examples of the liquid form food include cow's milk, wine, fruit juice, stock, yogurt, and the like, preferably cow's milk and fruit juice. Note that the "fruit juice" described above includes 100% juices such as orange juice. Regarding the liquid form food, it is preferable that the food itself is hydrophilic.

Note that the liquid component includes solutions and emulsions containing water as a functional material, and water itself (a functional material only).

<Method of Powderizing Liquid Component (Method of Producing Powder Composition)>

The present invention powderizes the liquid component by mixing the powderizing agent and the liquid component in the mixing step, and thereby produces a powder composition containing the powderized liquid component (hereinafter also referred to as the "powder composition"). The powderizing agent used in the production of the powder composition may be in the molten state (liquid form) or in the solid state (powder form). In the case of using one in the molten state, the cooling step to be described later is necessary. Note that if a powderizing agent in the solid state (powder form) is used, it is possible to skip this cooling step.

Hereinafter, a description is provided for a method of producing the powder composition.

<Mixing Step>

The powderizing agent to be subjected to the mixing step may be in the molten state (liquid form) or in the solid state (powder form), but is preferably used in the molten state. Use in the molten state makes it possible for the powderizing agent and the liquid component to mix well with each other, making it possible to obtain a more homogeneous powder composition.

No particular limitation is imposed on the mass ratio between the powderizing agent and the liquid component in the mixing step (powderizing agent:liquid component).

In addition, if the liquid component contains hydrophobic substances (preferably, if the solution itself of the hydrophobic substances is hydrophobic), the amount of the liquid component used may be, for example, 0.1 to 30% by mass, preferably 0.3 to 25% by mass, and more preferably 0.5 to 20% by mass relative to the total mass of the powder composition (final product). If the amount used is as described above, it is possible to more sufficiently powderize the liquid component.

If the liquid component contains hydrophilic substances (preferably, if the solution itself of the hydrophilic substances is hydrophilic), the amount of the liquid component used may be, for example, 0.1 to 300% by mass, preferably 0.3 to 250% by mass, and more preferably 0.5 to 200% by mass relative to the total mass of the powderizing agent (not the final product but the powderizing agent itself). If the mixing step is performed within the above-described mass ratio ranges, it is possible to more sufficiently powderize the liquid component. Note that in the calculation of the amount of the liquid component used, the amount of the "powderizing agent" described above does not include the trace amount of oil and/or fat powder of the powderizing agent added by the seeding process in order to simplify the calculation.

Although any known mixing means may be used as long as a homogeneous mixture is obtained, the mixing can be performed with, for example, a paddle mixer, an agi homo mixer, a disper mixer, and the like.

Regarding the mixing, the mixing may be performed under heating as necessary. In the case of using the powderizing agent in the molten state, the mixing temperature is, for example, 5 to 120° C., preferably 50 to 100° C., and more preferably 55 to 90° C. In the case of using the powderizing agent in the powder form, the mixing temperature is, for example, 5 to 40° C., preferably 10 to 30° C., and more preferably 15 to 25° C. Note that in the case of powderizing a particularly heat sensitive liquid component (for example, flavor, dye, vitamin, and the like), the mixing temperature is set to a temperature which does not cause decomposition or modification of the liquid component.

Although no particular limitation is imposed on the mixing time, the powderizing agent and the liquid component may be mixed until a sufficiently uniform mixture is formed, and the mixing time is, for example, 5 to 60 minutes, preferably 10 to 50 minutes, and more preferably 20 to 40 minutes.

<Cooling Step>

There is a case where the mixture of the powderizing agent and the liquid component is subsequently subjected to the cooling step for powderization. In particular, if an oil and/or fat composition in the molten state (liquid form) is used as the powderizing agent described above, the mixture is subjected to the cooling step for powderization because the state of the mixture is the liquid form. Note that if an oil and/or fat composition in the solid state (powder form) is used as the powderizing agent described above, the mixture is usually in the solid state (powder form), and the cooling step is an optional step performed as necessary.

The cooling step is the same as the cooling step used when obtaining the powder oil and/or fat composition explained in the paragraphs above and includes maintaining the mixture at a temperature lower than the melting point of the oil and/or fat composition contained in the powderizing agent. The "temperature lower than the melting point of the oil and/or fat composition" is, for example, a temperature lower than the melting point by 1 to 30° C., preferably a temperature lower than the melting point by 1 to 20° C., and more preferably a temperature lower than the melting point by 1 to 15° C.

If x (the number of carbon atoms of the fatty acid residue X) is 8 to 10, for example, the cooling of the mixture is performed such that the final temperature reaches a temperature of preferably 10 to 30° C., more preferably 15 to 25° C., and further preferably 18 to 22° C. For example, the final temperature in the cooling is preferably 30 to 40° C., more preferably 32 to 38° C., and further preferably 33 to 37° C. if x is 11 or 12, preferably 40 to 50° C., more preferably 42 to 48° C., and further preferably 44 to 47° C. if x is 13 or 14, preferably 50 to 60° C., more preferably 52 to 58° C., and further preferably 54 to 57° C. if x is 15 or 16, preferably 60 to 70° C., more preferably 62 to 68° C., and further preferably 64 to 67° C. if x is 17 or 18, and preferably 70 to 80° C., more preferably 72 to 78° C., and further preferably 74 to 77° C. if x is 19 or 20.

It is appropriate to allow the mixture to stand at the final temperature described above for preferably 120 minutes or more, more preferably 240 minutes or more, and further preferably 6 hours to 2 days, for example.

<Step of Promoting Powderization (Seeding Method, Tempering Method, and/or Pre-Cooling Method)>

For the purpose of promoting the powderization in the cooling step, the seeding process, the tempering process, and/or pre-cooling process may be performed as an optional step for promoting powderization between the mixing step and the cooling step.

Here, "between the mixing step and the cooling step" has a meaning which includes within the mixing step and after the mixing step, and before the cooling step and within the cooling step.

As the seeding process, it is possible to use the seeding process (c1) described above in relation to the production of the powder oil and/or fat composition constituting the powderizing agent.

As the tempering process, it is possible to use the tempering process (c2) described above in relation to the production of the powder oil and/or fat composition constituting the powderizing agent.

As the pre-cooling process, it is possible to use the pre-cooling process (c3) described above in relation to the production of the powder oil and/or fat composition constituting the powderizing agent.

<Drying Step>

Although the product after the mixing step or the cooling step is formed into powder without being subjected to a particular step (for example, by adding a weak impact), a drying step may be performed as an optional step for more promoting powderization. The drying step is particularly useful if the liquid component is a solution or an emulsion of the functional materials and the content of the solvent of the solution or of the dispersion medium of the emulsion is high (for example, the content of the solvent or the dispersion medium is 50 to 90% by mass relative to the total mass of the liquid component).

The temperature employed in the drying step may be a temperature which can evaporate the solvent or the dispersion medium described above and is, for example, 10 to 70° C., preferably 15 to 60° C., and more preferably 20 to 50° C.

Note that the production method of the present invention does not use a drying step which employs a temperature that could cause decomposition or modification of the liquid component. The drying step is performed at a temperature which does not cause decomposition or modification of the liquid component in the case of powderizing a particularly heat sensitive liquid component (for example, flavor, dye, vitamin, and the like).

Note that if the seeding process, the tempering process, and/or the pre-cooling process are performed, the drying step is preferably performed after the seeding process, the tempering process, and/or the pre-cooling process.

<Pulverization Step>

The product after the mixing step or the cooling step is a solid having voids with an increased volume. For this reason, without a particular step (for example, by applying a weak impact), the solid easily collapses, is pulverized, and formed into a powder form. Thus, although active pulverization means is not necessary, a pulverization step may be performed as an optional step.

The pulverization means may be strong machine pulverization means using spraying or a pulverizer (a mill and the like), but means of applying a weak impact (vibration) is sufficient. Although the means of applying a weak impact (vibration) is not particularly limited, means of applying weak vibration (impact) for pulverization (loosening) by, for example, shaking or sieving is preferable because of its simplicity.

Although the present invention does not intend to be bound by a particular theory, use of the powderizing agent of the present invention makes it possible to easily powderize the liquid component presumably because of the constitution of the oil and/or fat composition contained in the powderizing agent. To be more specific, we consider as follows. In the case of only the XXX-type triglyceride having equal chain lengths, the oil and/or fat crystal is packed very densely to become continuous, and crystallizes while maintaining a dense state. In the actual situation, since there is a small amount of the X2Y-type triglyceride having a long chain length of one fatty acid, the X2Y-type triglyceride enters the oil and/or fat crystal made up of the XXX-type triglyceride when the X2Y-type triglyceride cools and crystallizes from the molten state, which hinders the continuation of the XXX-type triglyceride for crystal growth, followed by crystallization in a very hollowly state (state where the volume has increased and voids have been formed) as a result. Here, the liquid component is taken in the voids to become a solid. Thus, powderization is achieved. It is considered that the liquid component is also taken in the voids by adding the powderizing agent in the powder form to the liquid component. The obtained solid has the form of an aggregate of the oil and/or fat composition having the liquid component taken therein, fragilely collapses by a weak impact, and is easily formed into powder.

<Characteristics of Powder Composition>

The powder composition obtained by applying the powderizing agent of the present invention to the liquid component is a solid in the form of powder at room temperature (20° C.).

The loose bulk density of the powder composition is 0.1 to 0.9 g/cm$^3$, preferably 0.15 to 0.85 g/cm$^3$, and more preferably 0.2 to 0.8 g/cm$^3$.

Here, the "loose bulk density" is the bulk density of a powder body which has freely fallen. The measurement of the loose bulk density (g/cm$^3$) can be obtained as follow. For example, a graduated cylinder having an inner diameter of 15 mm×25 mL is loosely filled with an appropriate amount of the powder composition allowed to fall from about 2 cm above the upper open end of the graduated cylinder. Then, the packed mass (g) is measured and the volume (mL) is read. Finally, the mass (g) of the powder composition per mL is calculated. In addition, the loose bulk density can be calculated by using a bulk specific gravity measurement apparatus of Kuramochi Kagakukikai Seisakusho and using a bulk specific gravity measured based on JIS K-6720 (or ISO 1060-1 and -2). To be more specific, 120 mL of sample is allowed to fall onto a receiver (100 mL cylindrical container having an inner diameter of 40 mm×height 85 mm) from a position higher by 38 mm than the upper open end of the receiver. A portion of the sample sticking out of the receiver is removed, and the mass (A g) of the sample corresponding to the internal volume of the receiver (100 mL) is weighed. The loose bulk density can be obtained by the following formula.

loose bulk density(g/mL)=$A$ (g)/100 (mL)

It is preferable that the measurement is performed three times and the average value thereof is taken.

In addition, the powder composition has the form of, for example, a spherical crystal or a plate-shaped crystal, and usually has the form of a plate-shaped crystal. In addition, the powder composition has an average particle diameter of, for example, 50 to 400 µm, preferably 50 to 300 µm, more preferably 50 to 250 µm, and especially preferably 100 to 200 µm. Here, the average particle diameter can be obtained with a particle size distribution measurement apparatus (for example, Microtrac MT 3300 ExII manufactured by Nikkiso Co., Ltd.) based on the laser diffraction scattering method (ISO 133201 and ISO 9276-1).

The expansion ratio of the powder composition is, for example, 1.0 to 6.0, preferably 1.2 to 5.5, and more preferably 1.5 to 5.0. An expansion ratio of 2.0 or more is preferable from the viewpoint that, for example, it is easy to take the liquid component in for powderization because a sufficient amount of void is contained in the powder composition. Here, the expansion ratio is represented as a ratio of the height of the vertex of the powderized composition after powderization to the height of the melt of the liquid component and the powderizing agent before powderization.

<Use of Powder Composition>

The powder composition obtained by applying the powderizing agent of the present invention to the liquid component can be used in various products without particular limitation depending on the functions provided by the functional materials contained in the powderized liquid component.

Specific examples of the products include, for example, foods and/or beverages, cosmetics, quasi drug, pharmaceutical drugs, household goods, feeds, general goods, agricultural chemicals, industrial chemical products, and the like.

In addition, the powder composition itself may be used as a product (for example, powdered food) and may be used as a raw material or an intermediate of the above-described product.

<Foods and/or Beverages>

The present invention also relates to foods and/or beverages particularly containing the powder composition described above. The foods and/or beverages include, for example, luxury foods without particular limitation.

Regarding the luxury foods, it is possible to use ones which can be blended with the powder composition of the present invention without particular limitation. Examples include cooking materials, processed foods, cooked foods, and the like. Specific examples include oils and/or fats or processed oils and/or fats (for example, deep frying oil for business use or household use, stir frying oil, spray oil, baking tray oil, margarine, fat spread, shortening, flour paste, creams, powder oils and/or fats, emulsified oils and/or fats, and the like), instant foods (for example, instant noodles, cup noodles, instant soups and stews, and the like), retort foods and canned foods (for example, curry, soup, stews, pasta sauce, prepared Chinese foods, prepared donburi, and the like), functional foods (for example, high-calorie beverages, fluid diets, balanced nutrition foods, dietary supplements, food for specified health uses, and the like), wheat flour or starch foods (for example, bread, pastas such as macaroni and spaghetti, pizza pies, noodles, cake mixes, processed cooked rice, serials, and the like), confectionery and desserts (for example, caramel, candies, chewing gum, chocolate, cookies and biscuits, cakes, pies, snacks, crackers, wagashi, beika, mamegashi, jellies, pudding, and the like), basic seasonings (for example, soy sauce, miso, sauces, and the like), flavor enhancers (curry or roux for stew, tare sauces, dressings, mayonnaise-like seasoning, noodle soup base, soup base for nabemono, chili oil, mustard, karashi, wasabi, grated ginger, grated onion, prepared kimchi, demi-glace, white sauce, tomato sauce, and the like), dairy products (for example, milk, processed milk, yogurts, lactic acid bacteria beverages, cheeses, ice creams, powdered infant formula, creams, and the like), processed marine products (for example, canned marine products, fish ham or sausage, pastes of marine product, canned oil immersed fish, and the like), processed agricultural products (for example, peanut butter, jam, marmalade, chocolate cream, processed menma products, processed zha cai products, nerigoma, sesame paste, and the like), processed livestock products (for example, animal meat ham or sausage, canned animal meat, pastes, hamburg steak, meatballs, flavored canned animal meat, and the like), cooked or half cooked foods (for example, frozen foods, refrigerated foods, packed side dishes, side dishes for storefront sale, and the like). In addition, the foods and/or beverages containing the powder composition of the present invention may be foods and/or beverages used for non-humans, for example pet foods for pets and feeds for livestock.

Next, the effects of the present invention are described in detail using Examples, but the present invention is not limited to Examples.

EXAMPLES

Preparation of Powderizing Agent

The powderizing agents A or A' and B described below were prepared.

Powderizing Agent A or A'

Into a 500-mL four-necked flask equipped with a stirrer, a thermometer, a nitrogen gas inlet tube, and a water separator, 44.1 g (0.479 mol) of glycerin (manufactured by Sakamoto Yakuhin Kogyo Co., Ltd.), 25.9 g (0.091 mol) of stearic acid (Palmac 98-18 (manufactured by Acidchem International Sdn Bhd)), and 266.0 g (1.544 mol) of capric acid (Palmac 99-10 (manufactured by Acidchem International Sdn Bhd)) were placed. These were reacted under a nitrogen stream at a temperature of 250° C. for 15 hours. Excessive capric acid was distilled off at 190° C. under reduced pressure, followed by bleaching, filtration, and deodorization. Thus, 245 g of a pale yellow liquid reaction product at 50° C. was obtained (XXX type: 80.6% by mass, X2Y type: 17.3% by mass). An oil and/or fat composition was prepared by mixing 60 g of the obtained reaction product with 140 g of tricaprin (manufactured by The Nisshin OilliO Group, Ltd.).

When the total triglyceride content is set to 100% by mass, the obtained oil and/or fat composition was an oil and/or fat composition containing 94.0% by mass of the XXX-type triglyceride having fatty acid residues X, each with x (x=10) carbon atoms, at positions 1 to 3 and 5.2% by mass of one or more types of the X2Y-type triglycerides each having a fatty acid residue Y with y (y=18) carbon atoms in place of one of the fatty acid residues X of the XXX-type triglyceride.

In addition, the melting point of this oil and/or fat composition was about 28° C. This oil and/or fat composition, when optionally subjected to heating and melting, transforms into the liquid state (liquid form).

This oil and/or fat composition was used as the powderizing agent A.

Moreover, a portion of this oil and/or fat composition was cooled in a 27° C.-thermostatic chamber until the product temperature reached 27° C. After that, tricaprin (manufactured by Nisshin OilliO Group, Ltd.) was cooled for solidification using liquid nitrogen, and 0.1% by mass of the oil and/or fat powder, pulverized with a freeze pulverizer (manufactured by AS ONE Corporation), was added to the remaining oil and/or fat composition (seeding process). The resultant was allowed to stand for 6 hours in the 20° C.-thermostatic chamber to form a solid having voids with an increased volume, followed by loosening. Thus, an oil and/or fat composition in the solid state (powder form) was obtained (loose bulk density: 0.2 g/cm$^3$, average particle diameter of 75 μm). This oil and/or fat composition was used as the powderizing agent A'.

Powderizing Agent B

Into a 500-mL four-necked flask equipped with a stirrer, a thermometer, a nitrogen gas inlet tube, and a water separator, 38.8 g (0.421 mol) of glycerin (manufactured by Sakamoto Yakuhin Kogyo Co., Ltd.), 26.2 g (0.092 mol) of stearic acid (Palmac 98-18 (manufactured by Acidchem International Sdn Bhd)), and 271.3 g (1.354 mol) of lauric acid (Palmac 98-12 (manufactured by Acidchem International Sdn Bhd)) were placed. These were reacted under a nitrogen stream at a temperature of 250° C. for 15 hours. Excessive lauric acid was distilled off at 220° C. under reduced pressure, followed by bleaching, filtration, and deodorization. Thus, 242 g of a pale yellow liquid reaction product at 50° C. was obtained (78.3% by mass, X2Y type: 19.2% by mass). An oil and/or fat composition was prepared by mixing 60 g of the obtained reaction product with 140 g of trilaurin (manufactured by The Nisshin OilliO Group, Ltd.).

When the total triglyceride content is set to 100% by mass, the obtained oil and/or fat composition was an oil and/or fat composition containing 93.1% by mass of the XXX-type triglyceride having fatty acid residues X, each with x (x=12) carbon atoms, at positions 1 to 3 and 5.8% by mass of one or more types of the X2Y-type triglycerides each having a fatty acid residue Y with y (y=18) carbon atoms in place of one of the fatty acid residues X of the XXX-type triglyceride.

In addition, the melting point of this oil and/or fat composition was about 45° C. This oil and/or fat composition, when subjected to heating and melting, transforms into the liquid state (liquid form).

This oil and/or fat composition was used as the powderizing agent B.

Loose Bulk Density

The loose bulk density was calculated by using a bulk specific gravity measurement apparatus of Kuramochi Kagakukikai Seisakusho and using a bulk specific gravity measured based on JIS K-6720 (or ISO 1060-1 and -2). To be more specific, 120 mL of sample was allowed to fall onto a receiver (100 mL cylindrical container having an inner diameter of 40 mm×height 85 mm) from a position higher by 38 mm than the upper open end of the receiver. Subsequently, a portion of the sample sticking out of the receiver was removed, and the mass (A g) of the sample corresponding to the internal volume of the receiver (100 mL) was weighed. The loose bulk density was obtained by the following formula.

loose bulk density (g/mL)=$A$ (g)/100 (mL)

The measurement was performed three times and the average value thereof was set to the measurement value.

Average Particle Diameter

The average particle diameter was measured with Microtrac MT 3300 ExII manufactured by Nikkiso Co., Ltd. based on the laser diffraction scattering method (ISO 133201 and ISO 9276-1).

Expansion Ratio

The expansion ratio was measured as a ratio of the height of the vertex after powderization to the height at the time of complete dissolution.

Examples 1 to 3 employed limonene (hydrophobic flavor) as the liquid component.

Example 1

Into a LABORAN screw tube jar No. 7 (manufactured by AS ONE Corporation), 9.9 g of the powderizing agent A and 0.1 g of (R)-(+)-Limonene (manufactured by Kanto Chemical Co., Inc.) were placed. These were kept at 60° C. for 0.5 hours and completely melt for mixing. Here, the amount of the liquid component used was 1% by mass relative to the total mass of the powder composition (powderizing agent A+liquid component). Next, the mixture was cooled in a 10° C.-thermostatic chamber for 0.5 hours (tempering process) and then was allowed to stand in a 20° C.-thermostatic chamber for 12 hours. Thus, a powder composition having voids with an increased volume was obtained.

The characteristics of the obtained powder composition were as follows.

loose bulk density: 0.3 g/cm$^3$ average particle diameter: 121 μm expansion ratio: ×3.9

As illustrated in FIG. 1, the powder composition obtained in Example 1 was in the form of powder.

Example 2

Into a LABORAN screw tube jar No. 7 (manufactured by AS ONE Corporation), 9.7 g of the powderizing agent A and 0.3 g of (R)-(+)-Limonene (manufactured by Kanto Chemical Co., Inc.) were placed. These were kept at 60° C. for 0.5 hours and completely melt for mixing. Here, the amount of the liquid component used was 3% by mass relative to the total mass of the powder composition (powderizing agent A+liquid component). Next, the mixture was cooled in a 10° C.-thermostatic chamber for 0.5 hours (tempering process) and then was allowed to stand in a 20° C.-thermostatic chamber for 12 hours. Thus, a powder composition having voids with an increased volume was obtained.

The characteristics of the obtained powder composition were as follows.
loose bulk density: 0.3 g/cm$^3$
average particle diameter: 147 μm
expansion ratio: ×2.5

As illustrated in FIG. 1, the powder composition obtained in Example 2 was in the form of powder.

Example 3

Into a LABORAN screw tube jar No. 7 (manufactured by AS ONE Corporation), 9.5 g of the powderizing agent A and 0.5 g of (R)-(+)-Limonene (manufactured by Kanto Chemical Co., Inc.) were placed. These were kept at 60° C. for 0.5 hours and completely melt for mixing. Here, the amount of the liquid component used was 5% by mass relative to the total mass of the powder composition (powderizing agent A+liquid component). Next, the mixture was cooled in a 10° C.-thermostatic chamber for 0.5 hours (tempering process) and then was allowed to stand in a 20° C.-thermostatic chamber for 12 hours. Thus, a powder composition having voids with an increased volume was obtained.

The characteristics of the obtained powder composition were as follows.
loose bulk density: 0.4 g/cm$^3$
average particle diameter: 198 μm
expansion ratio: ×1.6

As illustrated in FIG. 1, the powder composition obtained in Example 3 was in the form of powder.

Examples 4 to 6 employed vanillin (hydrophobic flavor) as the liquid component.

Example 4

Into a LABORAN screw tube jar No. 7 (manufactured by AS ONE Corporation), 9.9 g of the powderizing agent A and 0.1 g of Vanillin (manufactured by Wako Pure Chemical Industries, Ltd.) were placed. These were kept at 60° C. for 0.5 hours and completely melt for mixing. Here, the amount of the liquid component used was 1% by mass relative to the total mass of the powder composition (powderizing agent A+liquid component). Next, the mixture was cooled in a 10° C.-thermostatic chamber for 0.5 hours (tempering process) and then was allowed to stand in a 20° C.-thermostatic chamber for 12 hours. Thus, a powder composition having voids with an increased volume was obtained.

The characteristics of the obtained powder composition were as follows.
loose bulk density: 0.3 g/cm$^3$
average particle diameter: 116 μm
expansion ratio: ×4.0

Figure 2:
FIG. 2 is a view illustrating powder compositions obtained in Examples 4 to 6.

As illustrated in FIG. 2, the powder composition obtained in Example 4 was in the form of powder.

Example 5

Into a LABORAN screw tube jar No. 7 (manufactured by AS ONE Corporation), 9.7 g of the powderizing agent A and 0.3 g of Vanillin (manufactured by Wako Pure Chemical Industries, Ltd.) were placed. These were kept at 60° C. for 0.5 hours and completely melt for mixing. Here, the amount of the liquid component used was 3% by mass relative to the total mass of the powder composition (powderizing agent A+liquid component). Next, the mixture was cooled in a 10° C.-thermostatic chamber for 0.5 hours (tempering process) and then was allowed to stand in a 20° C.-thermostatic chamber for 12 hours. Thus, a powder composition having voids with an increased volume was obtained.

The characteristics of the obtained powder composition were as follows.
loose bulk density: 0.3 g/cm$^3$
average particle diameter: 139 μm
expansion ratio: ×2.7

As illustrated in FIG. 2, the powder composition obtained in Example 5 was in the form of powder.

Example 6

Into a LABORAN screw tube jar No. 7 (manufactured by AS ONE Corporation), 9.5 g of the powderizing agent A and 0.5 g of Vanillin (manufactured by Wako Pure Chemical Industries, Ltd.) were placed. These were kept at 60° C. for 0.5 hours and completely melt for mixing. Here, the amount of the liquid component used was 5% by mass relative to the total mass of the powder composition (powderizing agent A+liquid component). Next, the mixture was cooled in a 10° C.-thermostatic chamber for 0.5 hours (tempering process) and then was allowed to stand in a 20° C.-thermostatic chamber for 12 hours. Thus, a powder composition having voids with an increased volume was obtained.

The characteristics of the obtained powder composition were as follows.
loose bulk density: 0.3 g/cm$^3$
average particle diameter: 140 μm
expansion ratio: ×2.9

As illustrated in FIG. 2, the powder composition obtained in Example 6 was in the form of powder.

Examples 7 to 9 employed an orange dye (hydrophobic dye) as the liquid component.

Example 7

Into SV-110 (manufactured by Nichiden-Rika Glass Co., Ltd.), 9.9 g of the powderizing agent A and 0.1 g of Orange Color-500-OIL-EX being an orange dye (manufactured by Kiriya Chemical Co., Ltd.) (composition: 60% by mass of capsicum pepper dye (color value 2550), 1% by mass of extracted tocopherol, and 39% by mass of edible oil and/or fat) (extracted tocopherol and edible oil and/or fat are each the solvent of the orange dye) were placed. These were kept at 60° C. for 0.5 hours and completely melt for mixing. Here, the amount of the liquid component used was 1% by mass relative to the total mass of the powder composition (powderizing agent A+liquid component). Next, the mixture was cooled in a 10° C.-thermostatic chamber for 0.5 hours (tempering process) and then was allowed to stand in a 20° C.-thermostatic chamber for 12 hours. Thus, a powder composition having voids with an increased volume was obtained.

The characteristics of the obtained powder composition were as follows.
loose bulk density: 0.3 g/cm$^3$
average particle diameter: 110 μm
expansion ratio: ×3.6

Figure 3:
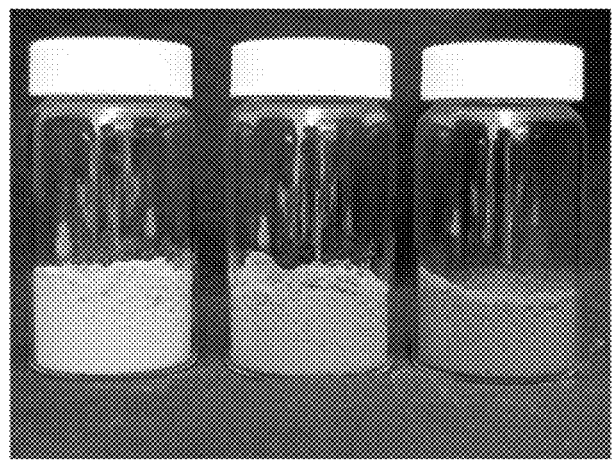
FIG. 3 is a view illustrating powder compositions obtained in Examples 7 to 9.

As illustrated in FIG. 3, the powder composition obtained in Example 7 was in the form of powder.

Example 8

Into SV-110 (manufactured by Nichiden-Rika Glass Co., Ltd.), 9.5 g of the powderizing agent A and 0.5 g of Orange Color-500-OIL-EX (manufactured by Kiriya Chemical Co., Ltd.) (composition: 60% by mass of capsicum pepper dye (color value 2550), 1% by mass of extracted tocopherol, and 39% by mass of edible oil and/or fat) were placed. These were kept at 60° C. for 0.5 hours and completely melt for mixing. Here, the amount of the liquid component used was 5% by mass relative to the total mass of the powder composition (powderizing agent A+liquid component). Next, the mixture was cooled in a 10° C.-thermostatic chamber for 0.5 hours (tempering process) and then was allowed to stand in a 20° C.-thermostatic chamber for 12 hours. Thus, a powder composition having voids with an increased volume was obtained.

The characteristics of the obtained powder composition were as follows.
loose bulk density: 0.3 g/cm$^3$
average particle diameter: 121 μm
expansion ratio: ×3.5

As illustrated in FIG. 3, the powder composition obtained in Example 8 was in the form of powder.

Example 9

Into SV-110 (manufactured by Nichiden-Rika Glass Co., Ltd.), 9.0 g of the powderizing agent A and 1.0 g of Orange Color-500-OIL-EX (manufactured by Kiriya Chemical Co., Ltd.) (composition: 60% by mass of capsicum pepper dye (color value 2550), 1% by mass of extracted tocopherol, and 39% by mass of edible oil and/or fat) were placed. These were kept at 60° C. for 0.5 hours and completely melt for mixing. Here, the amount of the liquid component used was 10% by mass relative to the total mass of the powder composition (powderizing agent A+liquid component). Next, the mixture was cooled in a 10° C.-thermostatic chamber for 0.5 hours (tempering process) and then was allowed to stand in a 20° C.-thermostatic chamber for 12 hours. Thus, a powder composition having voids with an increased volume was obtained.

The characteristics of the obtained powder composition were as follows.
loose bulk density: 0.3 g/cm$^3$
average particle diameter: 136 μm
expansion ratio: ×3.3

As illustrated in FIG. 3, the powder composition obtained in Example 9 was in the form of powder.

Examples 10 to 12 employed roasted shrimp oil (hydrophobic flavor) as the liquid component.

Example 10

Into a LABORAN screw tube jar No. 6 (manufactured by AS ONE Corporation), 2.97 g of the powderizing agent B and 0.03 g of roasted shrimp oil #1264 (manufactured by Takata Koryo Co., Ltd.) (composition: 90% by mass of MCT (medium-chain triglyceride) and 10% by mass of flavor base (shrimp base: flavor and/or taste oil)) (MCT is the solvent of roasted shrimp oil) were placed. These were kept at 60° C. for 0.5 hours and completely melt for mixing. Here, the amount of the liquid component used was 1% by mass relative to the total mass of the powder composition (powderizing agent B+liquid component). Next, the mixture was cooled in a 28° C.-thermostatic chamber for 1 hour (tempering process) and then was allowed to stand in a 38° C.-thermostatic chamber for 12 hours. Thus, a powder composition having voids with an increased volume was obtained.

The characteristics of the obtained powder composition were as follows.
loose bulk density: 0.3 g/cm$^3$
average particle diameter: 149 μm
expansion ratio: ×3.9

Figure 4:
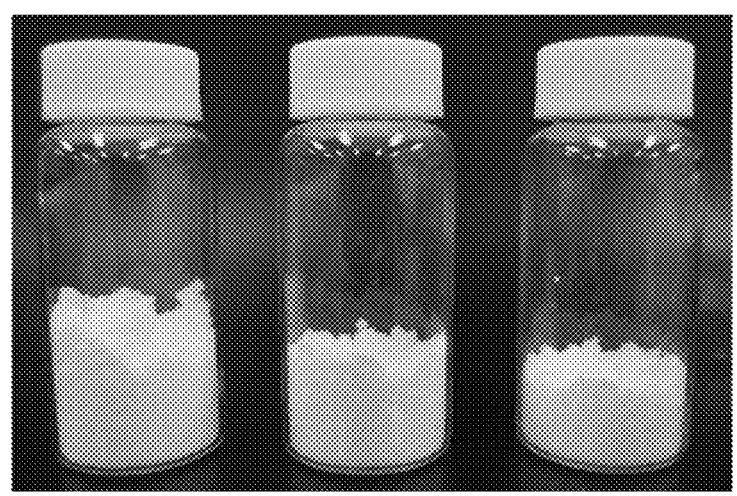
FIG. 4 is a view illustrating powder compositions obtained in Examples 10 to 12.

As illustrated in FIG. 4, the powder composition obtained in Example 10 was in the form of powder.

Example 11

Into a LABORAN screw tube jar No. 6 (manufactured by AS ONE Corporation), 2.85 g of the powderizing agent B and 0.15 g of roasted shrimp oil #1264 (manufactured by Takata Koryo Co., Ltd.) (composition: 90% by mass of MCT and 10% by mass of flavor base (shrimp base: flavor and/or taste oil)) were placed. These were kept at 60° C. for 0.5 hours and completely melt for mixing. Here, the amount of the liquid component used was 5% by mass relative to the total mass of the powder composition (powderizing agent B+liquid component). Next, the mixture was cooled in a 28° C.-thermostatic chamber for 1 hour (tempering process) and then was allowed to stand in a 38° C.-thermostatic chamber for 12 hours. Thus, a powder composition having voids with an increased volume was obtained.

The characteristics of the obtained powder composition were as follows.
loose bulk density: 0.3 g/cm$^3$
average particle diameter: 168 μm
expansion ratio: ×3.0

As illustrated in FIG. 4, the powder composition obtained in Example 11 was in the form of powder.

Example 12

Into a LABORAN screw tube jar No. 6 (manufactured by AS ONE Corporation), 2.7 g of the powderizing agent B and 0.3 g of roasted shrimp oil #1264 (manufactured by Takata Koryo Co., Ltd.) (composition: 90% by mass of MCT and 10% by mass of flavor base (shrimp base: flavor and/or taste oil)) were placed. These were kept at 60° C. for 0.5 hours and completely melt for mixing. Here, the amount of the liquid component used was 10% by mass relative to the total mass of the powder composition (powderizing agent B+liquid component). Next, the mixture was cooled in a 28° C.-thermostatic chamber for 1 hour (tempering process) and then was allowed to stand in a 38° C.-thermostatic chamber for 12 hours. Thus, a powder composition having voids with an increased volume was obtained.

The characteristics of the obtained powder composition were as follows.
loose bulk density: 0.3 g/cm$^3$
average particle diameter: 170 μm
expansion ratio: ×2.9

As illustrated in FIG. 4, the powder composition obtained in Example 12 was in the form of powder.

Examples 13 to 15 employed onion oil (hydrophobic flavor) as the liquid component.

Example 13

Into a LABORAN screw tube jar No. 6 (manufactured by AS ONE Corporation), 2.97 g of the powderizing agent B and 0.03 g of onion oil CA (manufactured by Fuji Foods Corporation) (composition: 99.9% by mass of flavor and/or taste base (extracted raw material and plant oil and/or fat) and 0.1% by mass of antioxidant) were placed. These were kept at 60° C. for 0.5 hours and completely melt for mixing.

Here, the amount of the liquid component used was 1% by mass relative to the total mass of the powder composition (powderizing agent B+liquid component). Next, the mixture was cooled in a 28° C.-thermostatic chamber for 1 hour (tempering process) and then was allowed to stand in a 38° C.-thermostatic chamber for 12 hours. Thus, a powder composition having voids with an increased volume was obtained.

The characteristics of the obtained powder composition were as follows.
- loose bulk density: 0.3 g/cm$^3$
- average particle diameter: 111 μm
- expansion ratio: ×5.4

Figure 5:
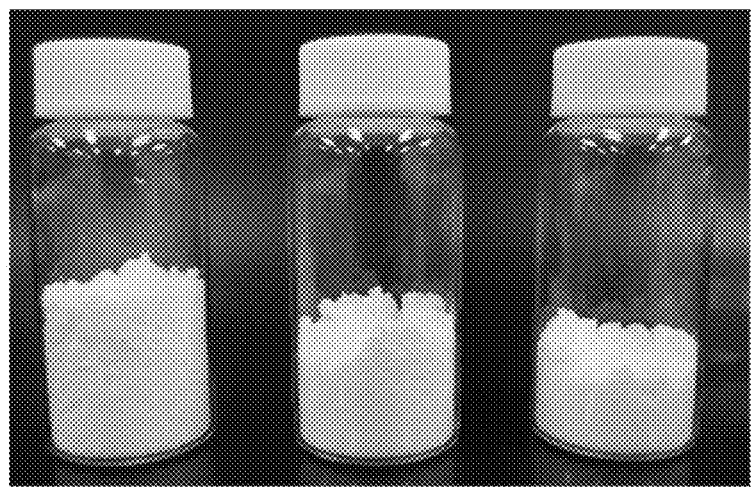
FIG. 5 is a view illustrating powder compositions obtained in Examples 13 to 15.

As illustrated in FIG. 5, the powder composition obtained in Example 13 was in the form of powder.

Example 14

Into a LABORAN screw tube jar No. 6 (manufactured by AS ONE Corporation), 2.85 g of the powderizing agent B and 0.15 g of onion oil CA (manufactured by Fuji Foods Corporation) (composition: 99.9% by mass of flavor and/or taste base (extracted raw material and plant oil and/or fat) and 0.1% by mass of antioxidant) were placed. These were kept at 60° C. for 0.5 hours and completely melt for mixing. Here, the amount of the liquid component used was 5% by mass relative to the total mass of the powder composition (powderizing agent B+liquid component). Next, the mixture was cooled in a 28° C.-thermostatic chamber for 1 hour (tempering process) and then was allowed to stand in a 38° C.-thermostatic chamber for 12 hours. Thus, a powder composition having voids with an increased volume was obtained.

The characteristics of the obtained powder composition were as follows.
- loose bulk density: 0.3 g/cm$^3$
- average particle diameter: 137 μm
- expansion ratio: ×3.9

As illustrated in FIG. 5, the powder composition obtained in Example 14 was in the form of powder.

Example 15

Into a LABORAN screw tube jar No. 6 (manufactured by AS ONE Corporation), 2.7 g of the powderizing agent B and 0.3 g of onion oil CA (manufactured by Fuji Foods Corporation) (composition: 99.9% by mass of flavor and/or taste base (extracted raw material and plant oil and/or fat) and 0.1% by mass of antioxidant) were placed. These were kept at 60° C. for 0.5 hours and completely melt for mixing. Here, the amount of the liquid component used was 10% by mass relative to the total mass of the powder composition (powderizing agent B+liquid component). Next, the mixture was cooled in a 28° C.-thermostatic chamber for 1 hour (tempering process) and then was allowed to stand in a 38° C.-thermostatic chamber for 12 hours. Thus, a powder composition having voids with an increased volume was obtained.

The characteristics of the obtained powder composition were as follows.
- loose bulk density: 0.3 g/cm$^3$
- average particle diameter: 149 μm
- expansion ratio: ×2.9

As illustrated in FIG. 5, the powder composition obtained in Example 15 was in the form of powder.

Examples 16 to 18 employed vitamin E (hydrophobic vitamin) as the liquid component.

Example 16

Into a LABORAN screw tube jar No. 6 (manufactured by AS ONE Corporation), 2.97 g of the powderizing agent B and 0.03 g of E-Mix D (vitamin E) (manufactured by Eisai Co., Ltd.) were placed. These were kept at 60° C. for 0.5 hours and completely melt for mixing. Here, the amount of the liquid component used was 1% by mass relative to the total mass of the powder composition (powderizing agent B+liquid component). Next, the mixture was cooled in a 28° C.-thermostatic chamber for 1 hour (tempering process) and then was allowed to stand in a 38° C.-thermostatic chamber for 12 hours. Thus, a powder composition having voids with an increased volume was obtained.

The characteristics of the obtained powder composition were as follows.
- loose bulk density: 0.3 g/cm$^3$
- average particle diameter: 107 μm
- expansion ratio: ×5.1

Figure 6:
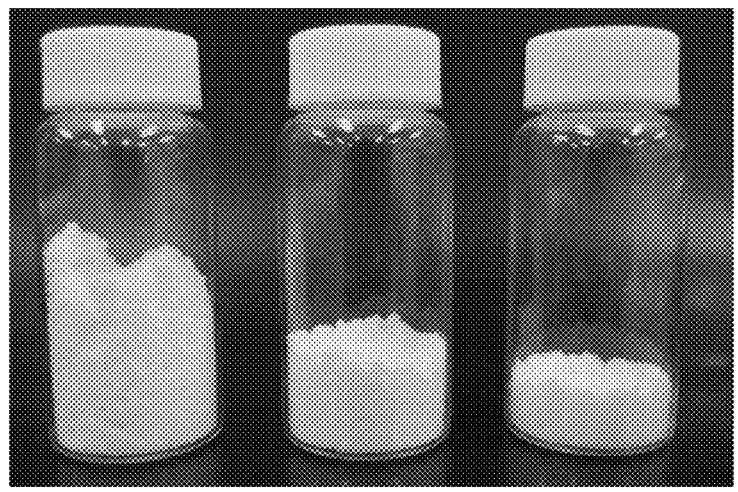
FIG. 6 is a view illustrating powder compositions obtained in Examples 16 to 18.

As illustrated in FIG. 6, the powder composition obtained in Example 16 was in the form of powder.

Example 17

Into a LABORAN screw tube jar No. 6 (manufactured by AS ONE Corporation), 2.85 g of the powderizing agent B and 0.15 g of E-Mix D (manufactured by Eisai Co., Ltd.) were placed. These were kept at 60° C. for 0.5 hours and completely melt for mixing. Here, the amount of the liquid component used was 5% by mass relative to the total mass of the powder composition (powderizing agent B+liquid component). Next, the mixture was cooled in a 28° C.-thermostatic chamber for 1 hour (tempering process) and then was allowed to stand in a 38° C.-thermostatic chamber for 12 hours. Thus, a powder composition having voids with an increased volume was obtained.

The characteristics of the obtained powder composition were as follows.
- loose bulk density: 0.3 g/cm$^3$
- average particle diameter: 151 μm
- expansion ratio: ×2.7

As illustrated in FIG. 6, the powder composition obtained in Example 17 was in the form of powder.

Example 18

Into a LABORAN screw tube jar No. 6 (manufactured by AS ONE Corporation), 2.7 g of the powderizing agent B and 0.3 g of E-Mix D (manufactured by Eisai Co., Ltd.) were placed. These were kept at 60° C. for 0.5 hours and completely melt for mixing. Here, the amount of the liquid component used was 10% by mass relative to the total mass of the powder composition (powderizing agent B+liquid component). Next, the mixture was cooled in a 28° C.-thermostatic chamber for 1 hour (tempering process) and then was allowed to stand in a 38° C.-thermostatic chamber for 12 hours. Thus, a powder composition having voids with an increased volume was obtained.

The characteristics of the obtained powder composition were as follows.
- loose bulk density: 0.3 g/cm$^3$
- average particle diameter: 190 μm
- expansion ratio: ×1.7

As illustrated in FIG. 6, the powder composition obtained in Example 18 was in the form of powder.

Examples 19 to 23 employed lecithin (hydrophobic phospholipid) as the liquid component.

Example 19

Into a LABORAN screw tube jar No. 6 (manufactured by AS ONE Corporation), 2.97 g of the powderizing agent B and 0.03 g of SLP-Paste (lecithin) (manufactured by Tsuji Oil Mill Co., Ltd.) were placed. These were kept at 60° C. for 0.5 hours and completely melt for mixing. Here, the amount of the liquid component used was 1% by mass relative to the total mass of the powder composition (powderizing agent B+liquid component). Next, the mixture was cooled in a 28° C.-thermostatic chamber for 1 hour (tempering process) and then was allowed to stand in a 38° C.-thermostatic chamber for 12 hours. Thus, a powder composition having voids with an increased volume was obtained.

The characteristics of the obtained powder composition were as follows.
loose bulk density: 0.3 g/cm$^3$
average particle diameter: 123 μm
expansion ratio: ×4.7

Figure 7:
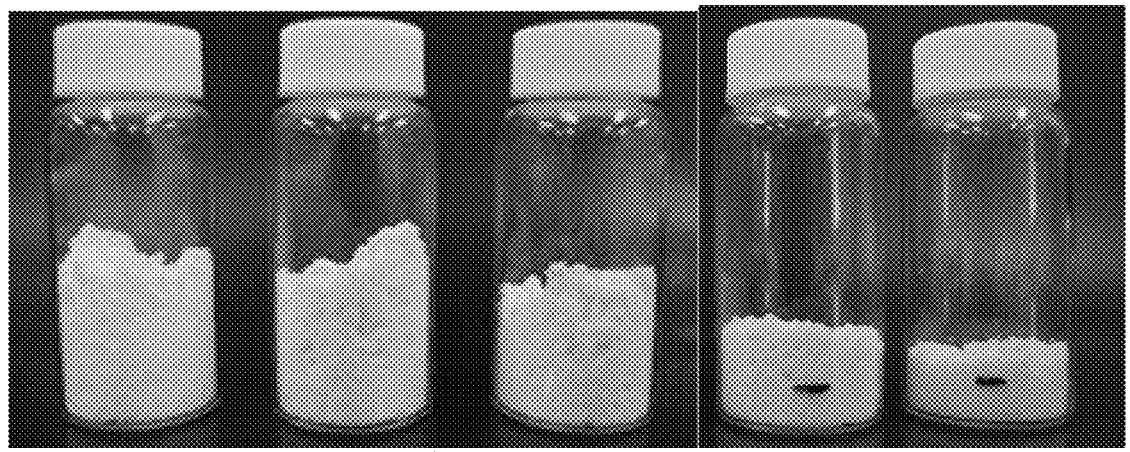
FIG. 7 is a view illustrating powder compositions obtained in Examples 19 to 23.

As illustrated in FIG. 7, the powder composition obtained in Example 19 was in the form of powder.

Example 20

Into a LABORAN screw tube jar No. 6 (manufactured by AS ONE Corporation), 2.85 g of the powderizing agent B and 0.15 g of SLP-Paste (manufactured by Tsuji Oil Mill Co., Ltd.) were placed. These were kept at 60° C. for 0.5 hours and completely melt for mixing. Here, the amount of the liquid component used was 5% by mass relative to the total mass of the powder composition (powderizing agent B+liquid component). Next, the mixture was cooled in a 28° C.-thermostatic chamber for 1 hour (tempering process) and then was allowed to stand in a 38° C.-thermostatic chamber for 12 hours. Thus, a powder composition having voids with an increased volume was obtained.

The characteristics of the obtained powder composition were as follows.
loose bulk density: 0.3 g/cm$^3$
average particle diameter: 119 μm
expansion ratio: ×4.9

As illustrated in FIG. 7, the powder composition obtained in Example 20 was in the form of powder.

Example 21

Into a LABORAN screw tube jar No. 6 (manufactured by AS ONE Corporation), 2.7 g of the powderizing agent B and 0.3 g of SLP-Paste (manufactured by Tsuji Oil Mill Co., Ltd.) were placed. These were kept at 60° C. for 0.5 hours and completely melt for mixing. Here, the amount of the liquid component used was 10% by mass relative to the total mass of the powder composition (powderizing agent B+liquid component). Next, the mixture was cooled in a 28° C.-thermostatic chamber for 1 hour (tempering process) and then was allowed to stand in a 38° C.-thermostatic chamber for 12 hours. Thus, a powder composition having voids with an increased volume was obtained.

The characteristics of the obtained powder composition were as follows.
loose bulk density: 0.3 g/cm$^3$
average particle diameter: 130 μm
expansion ratio: ×4.3

As illustrated in FIG. 7, the powder composition obtained in Example 21 was in the form of powder.

Example 22

Into a LABORAN screw tube jar No. 6 (manufactured by AS ONE Corporation), 2.4 g of the powderizing agent B and 0.6 g of SLP-Paste (manufactured by Tsuji Oil Mill Co., Ltd.) were placed. These were kept at 60° C. for 0.5 hours and completely melt for mixing. Here, the amount of the liquid component used was 20% by mass relative to the total mass of the powder composition (powderizing agent B+liquid component). Next, the mixture was cooled in a 28° C.-thermostatic chamber for 1 hour (tempering process) and then was allowed to stand in a 38° C.-thermostatic chamber for 12 hours. Thus, a powder composition having voids with an increased volume was obtained.

The characteristics of the obtained powder composition were as follows.
loose bulk density: 0.3 g/cm$^3$
average particle diameter: 176 μm
expansion ratio: ×2.6

As illustrated in FIG. 7, the powder composition obtained in Example 22 was in the form of powder.

Example 23

Into a LABORAN screw tube jar No. 6 (manufactured by AS ONE Corporation), 2.1 g of the powderizing agent B and 0.9 g of SLP-Paste (manufactured by Tsuji Oil Mill Co., Ltd.) were placed. These were kept at 60° C. for 0.5 hours and completely melt for mixing. Here, the amount of the liquid component used was 30% by mass relative to the total mass of the powder composition (powderizing agent B+liquid component). Next, the mixture was cooled in a 28° C.-thermostatic chamber for 1 hour (tempering process) and then was allowed to stand in a 38° C.-thermostatic chamber for 12 hours. Thus, a powder composition having voids with an increased volume was obtained.

The characteristics of the obtained powder composition were as follows.
loose bulk density: 0.4 g/cm$^3$
average particle diameter: 214 μm
expansion ratio: ×1.7

As illustrated in FIG. 7, the powder composition obtained in Example 23 was in the form of powder.

Examples 24 to 26 employed shrimp flavor (hydrophilic flavor) as the liquid component.

Example 24

Into a LABORAN screw tube jar No. 6 (manufactured by AS ONE Corporation), 3.00 g of the powderizing agent B and 0.03 g of shrimp flavor (manufactured by Takata Koryo Co., Ltd.) (composition: 50% by mass of ethanol, 30% by mass of purified water, 18% by mass of glycerin, and 2% by mass of flavor base) (ethanol, purified water, and glycerin are each the solvent of shrimp flavor) were placed. These were kept at 60° C. for 0.5 hours and completely melt for mixing. Here, the amount of the liquid component used was 1% by mass relative to the total mass of the powderizing agent (powderizing agent B). Next, the mixture was cooled in a 28° C.-thermostatic chamber for 1 hour (tempering process) and then was allowed to stand in a 38° C.-thermostatic chamber for 12 hours. Thus, a powder composition having voids with an increased volume was obtained.

The characteristics of the obtained powder composition were as follows.
  loose bulk density: 0.3 g/cm³
  average particle diameter: 163 μm
  expansion ratio: ×3.1

Figure 8:
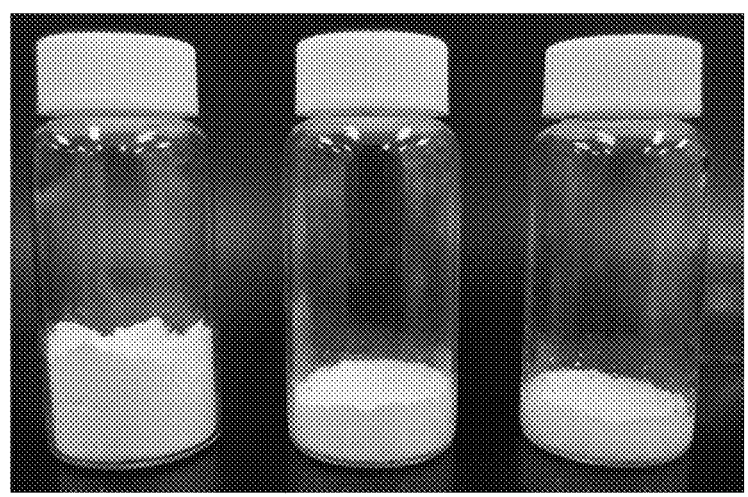
FIG. 8 is a view illustrating powder compositions obtained in Examples 24 to 26.

As illustrated in FIG. 8, the powder composition obtained in Example 24 was in the form of powder.

Example 25

Into a LABORAN screw tube jar No. 6 (manufactured by AS ONE Corporation), 3.00 g of the powderizing agent B and 0.15 g of shrimp flavor (manufactured by Takata Koryo Co., Ltd.) (composition: 50% by mass of ethanol, 30% by mass of purified water, 18% by mass of glycerin, and 2% by mass of flavor base) were placed. These were kept at 60° C. for 0.5 hours and completely melt for mixing. Here, the amount of the liquid component used was 5% by mass relative to the total mass of the powderizing agent (powderizing agent B). Next, the mixture was cooled in a 28° C.-thermostatic chamber for 1 hour (tempering process) and then was allowed to stand in a 38° C.-thermostatic chamber for 12 hours. Thus, a powder composition having voids with an increased volume was obtained.

The characteristics of the obtained powder composition were as follows.
  loose bulk density: 0.4 g/cm³
  average particle diameter: 188 μm
  expansion ratio: ×1.4

As illustrated in FIG. 8, the powder composition obtained in Example 25 was in the form of powder.

Example 26

Into a LABORAN screw tube jar No. 6 (manufactured by AS ONE Corporation), 3.00 g of the powderizing agent B and 0.3 g of shrimp flavor (manufactured by Takata Koryo Co., Ltd.) (composition: 50% by mass of ethanol, 30% by mass of purified water, 18% by mass of glycerin, and 2% by mass of flavor base) were placed. These were kept at 60° C. for 0.5 hours and completely melt for mixing. Here, the amount of the liquid component used was 10% by mass relative to the total mass of the powderizing agent (powderizing agent B). Next, the mixture was cooled in a 28° C.-thermostatic chamber for 1 hour (tempering process) and then was allowed to stand in a 38° C.-thermostatic chamber for 12 hours. Thus, a powder composition having voids with an increased volume was obtained.

The characteristics of the obtained powder composition were as follows.
  loose bulk density: 0.5 g/cm³
  average particle diameter: 184 μm
  expansion ratio: ×1.0

As illustrated in FIG. 8, the powder composition obtained in Example 26 was in the form of powder.

Examples 27 to 29 employed an orange dye (hydrophilic dye) as the liquid component.

Example 27

Into a LABORAN screw tube jar No. 6 (manufactured by AS ONE Corporation), 3.00 g of the powderizing agent B and 0.03 g of Orange Color 75 WS (manufactured by Kiriya Chemical Co., Ltd.) (composition: 15% by mass of capsicum pepper dye (color value 1400), 21.2% by mass of purified water, 55% by mass of glycerin, 4% by mass of glycerin fatty acid ester, 4% by mass of sucrose fatty acid ester, and 0.8% by mass of extracted tocopherol) (purified water and glycerin are each the solvent of orange dye, glycerin fatty acid ester and sucrose fatty acid ester are each an emulsifier, and extracted tocopherol is an antioxidant) were placed. These were kept at 60° C. for 0.5 hours and completely melt for mixing. Here, the amount of the liquid component used was 1% by mass relative to the total mass of the powderizing agent (powderizing agent B). Next, the mixture was cooled in a 28° C.-thermostatic chamber for 1 hour (tempering process) and then was allowed to stand in a 38° C.-thermostatic chamber for 12 hours. Thus, a powder composition having voids with an increased volume was obtained.

The characteristics of the obtained powder composition were as follows.
  loose bulk density: 0.3 g/cm³
  average particle diameter: 136 μm
  expansion ratio: ×3.3

Figure 9:
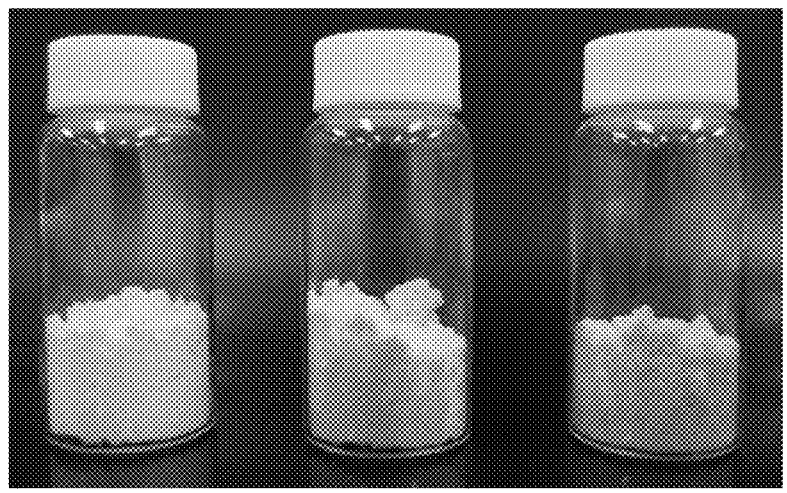
FIG. 9 is a view illustrating powder compositions obtained in Examples 27 to 29.

As illustrated in FIG. 9, the powder composition obtained in Example 27 was in the form of powder.

Example 28

Into a LABORAN screw tube jar No. 6 (manufactured by AS ONE Corporation), 3.00 g of the powderizing agent B and 0.15 g of Orange Color 75 WS (manufactured by Kiriya Chemical Co., Ltd.) (composition: 15% by mass of capsicum pepper dye (color value 1400), 21.2% by mass of purified water, 55% by mass of glycerin, 4% by mass of glycerin fatty acid ester, 4% by mass of sucrose fatty acid ester, and 0.8% by mass of extracted tocopherol) were placed. These were kept at 60° C. for 0.5 hours and completely melt for mixing. Here, the amount of the liquid component used was 5% by mass relative to the total mass of the powderizing agent (powderizing agent B). Next, the mixture was cooled in a 28° C.-thermostatic chamber for 1 hour (tempering process) and then was allowed to stand in a 38° C.-thermostatic chamber for 12 hours. Thus, a powder composition having voids with an increased volume was obtained.

The characteristics of the obtained powder composition were as follows.
  loose bulk density: 0.3 g/cm³
  average particle diameter: 110 μm
  expansion ratio: ×3.7

As illustrated in FIG. 9, the powder composition obtained in Example 28 was in the form of powder.

Example 29

Into a LABORAN screw tube jar No. 6 (manufactured by AS ONE Corporation), 3.00 g of the powderizing agent B and 0.3 g of Orange Color 75 WS (manufactured by Kiriya Chemical Co., Ltd.) (composition: 15% by mass of capsicum pepper dye (color value 1400), 21.2% by mass of purified water, 55% by mass of glycerin, 4% by mass of glycerin fatty acid ester, 4% by mass of sucrose fatty acid ester, and 0.8% by mass of extracted tocopherol) were placed. These were kept at 60° C. for 0.5 hours and completely melt for mixing. Here, the amount of the liquid component used was 10% by mass relative to the total mass of the powderizing agent (powderizing agent B). Next, the mixture was cooled in a 28° C.-thermostatic chamber for 1 hour (tempering process) and then was allowed to stand in a 38° C.-thermostatic chamber for 12 hours. Thus, a powder composition having voids with an increased volume was obtained.

The characteristics of the obtained powder composition were as follows.

loose bulk density: 0.3 g/cm$^3$ average particle diameter: 124 μm expansion ratio: ×3.0

As illustrated in FIG. 9, the powder composition obtained in Example 29 was in the form of powder.

Examples 30 to 32 employed water as the liquid component. Note that water colored with a dye was used in order to facilitate the observation of the change in water by the powderization treatment.

Example 30

After 6.0 g of the powderizing agent A was kept at 60° C. for 0.5 hours for complete melting and was cooled in a 27° C.-thermostatic chamber until the product temperature reached 27° C., the resultant was placed into a LABORAN screw tube jar No. 8 (manufactured by AS ONE Corporation) containing 0.06 g of the oil and/or fat powder of the powderizing agent A (used as the core (seed) of the seeding process) and 6.0 g of water colored with red (99.9% by mass of water and 0.1% by mass of edible dye Aka (manufactured by Kyoritsu Foods Co., Ltd.)). Both were mixed well and allowed to stand in a 20° C.-thermostatic chamber for 6 hours. Thus, a powder composition was obtained. Here, the amount of the liquid component used was 100% by mass relative to the total mass of the powderizing agent (powderizing agent A).

The characteristics of the obtained powder composition were as follows.

loose bulk density: 0.8 g/cm$^3$

Note that when the powder composition obtained as described above was dried at 20° C. for 24 hours, a powder composition having a loose bulk density of 0.4 g/cm$^3$ was obtained.

average particle diameter: 106 μm expansion ratio: ×1.6

Figure 10:
FIG. 10 is a view illustrating powder compositions obtained in Examples 30 to 32.

As illustrated in FIG. 10, the powder composition obtained in Example 30 (after drying) was in the form of powder.

Example 31

After 6.0 g of the powderizing agent A was kept at 60° C. for 0.5 hours for complete melting and was cooled in a 27° C.-thermostatic chamber until the product temperature reached 27° C., the resultant was placed into a LABORAN screw tube jar No. 8 (manufactured by AS ONE Corporation) containing 0.06 g of the oil and/or fat powder of the powderizing agent A (used as the core (seed) of the seeding process) and 12.0 g of water colored with red (99.9% by mass of water and 0.1% by mass of edible dye Aka (manufactured by Kyoritsu Foods Co., Ltd.)). Both were mixed well and allowed to stand in a 20° C.-thermostatic chamber for 6 hours. Thus, a powder composition was obtained. Here, the amount of the liquid component used was 200% by mass relative to the total mass of the powderizing agent (powderizing agent A).

The characteristics of the obtained powder composition were as follows.

loose bulk density: 0.8 g/cm$^3$

Note that when the powder composition obtained as described above was dried at 20° C. for 48 hours, a powder composition having a loose bulk density of 0.4 g/cm$^3$ was obtained.

average particle diameter: 104 μm expansion ratio: ×1.3

As illustrated in FIG. 10, the powder composition obtained in Example 31 (after drying) was in the form of powder.

Example 32

After 6.0 g of the powderizing agent A was kept at 60° C. for 0.5 hours for complete melting and was cooled in a 27° C.-thermostatic chamber until the product temperature reached 27° C., the resultant was placed into a LABORAN screw tube jar No. 8 (manufactured by AS ONE Corporation) containing 0.06 g of the oil and/or fat powder of the powderizing agent A (used as the core (seed) of the seeding process) and 18.0 g of water colored with red (99.9% by mass of water and 0.1% by mass of edible dye Aka (manufactured by Kyoritsu Foods Co., Ltd.)). Both were mixed well and allowed to stand in a 20° C.-thermostatic chamber for 6 hours. Thus, a powder composition was obtained. Here, the amount of the liquid component used was 300% by mass relative to the total mass of the powderizing agent (powderizing agent A).

The characteristics of the obtained powder composition were as follows.

loose bulk density: 0.9 g/cm$^3$

Note that when the powder composition obtained as described above was dried at 20° C. for 72 hours, a powder composition having a loose bulk density of 0.5 g/cm$^3$ was obtained.

average particle diameter: 112 μm expansion ratio: ×1.5

As illustrated in FIG. 10, the powder composition obtained in Example 32 (after drying) was in the form of powder.

Examples 33 to 35 employed cow's milk (liquid form food) as the liquid component.

Example 33

After 6.0 g of the powderizing agent A was kept at 60° C. for 0.5 hours for complete melting and was cooled in a 27° C.-thermostatic chamber until the product temperature reached 27° C., the oil and/or fat composition added with 0.06 g of the oil and/or fat powder of the powderizing agent A (used as the core (seed) of the seeding process) was placed into a LABORAN screw tube jar No. 8 (manufactured by AS ONE Corporation) containing 6.0 g of cow's milk (manufactured by Furuya Milk Products Co., Ltd.). Both were mixed well and allowed to stand in a 20° C.-thermostatic chamber for 6 hours. Thus, a powder composition was obtained. Here, the amount of the liquid component used was 100% by mass relative to the total mass of the powderizing agent (powderizing agent A).

The characteristics of the obtained powder composition were as follows.

loose bulk density: 0.9 g/cm$^3$

Note that when the powder composition obtained as described above was dried at 20° C. for 24 hours, a powder composition having a loose bulk density of 0.5 g/cm$^3$ was obtained.

average particle diameter: 102 μm expansion ratio: ×1.5

Figure 11:
FIG. 11 is a view illustrating powder compositions obtained in Examples 33 to 35.

As illustrated in FIG. 11, the powder composition obtained in Example 33 (after drying) was in the form of powder.

Example 34

After 6.0 g of the powderizing agent A was kept at 60° C. for 0.5 hours for complete melting and was cooled in a 27° C.-thermostatic chamber until the product temperature reached 27° C., the oil and/or fat composition added with 0.06 g of the oil and/or fat powder of the powderizing agent A (used as the core (seed) of the seeding process) was placed into a LABORAN screw tube jar No. 8 (manufactured by AS ONE Corporation) containing 12.0 g of cow's milk (manufactured by Furuya Milk Products Co., Ltd.). Both were mixed well and allowed to stand in a 20° C.-thermostatic chamber for 6 hours. Thus, a powder composition was obtained. Here, the amount of the liquid component used was 200% by mass relative to the total mass of the powderizing agent (powderizing agent A).

The characteristics of the obtained powder composition were as follows.

loose bulk density: 0.9 g/cm$^3$

Note that when the powder composition obtained as described above was dried at 20° C. for 48 hours, a powder composition having a loose bulk density of 0.5 g/cm$^3$ was obtained.

average particle diameter: 108 μm expansion ratio: ×1.3

As illustrated in FIG. 11, the powder composition obtained in Example 34 (after drying) was in the form of powder.

Example 35

After 6.0 g of the powderizing agent A was kept at 60° C. for 0.5 hours for complete melting and was cooled in a 27° C.-thermostatic chamber until the product temperature reached 27° C., the oil and/or fat composition added with 0.06 g of the oil and/or fat powder of the powderizing agent A (used as the core (seed) of the seeding process) was placed into a LABORAN screw tube jar No. 8 (manufactured by AS ONE Corporation) containing 18.0 g of cow's milk (manufactured by Furuya Milk Products Co., Ltd.). Both were mixed well and allowed to stand in a 20° C.-thermostatic chamber for 6 hours. Thus, a powder composition was obtained. Here, the amount of the liquid component used was 300% by mass relative to the total mass of the powderizing agent (powderizing agent A).

The characteristics of the obtained powder composition were as follows.

loose bulk density: 0.9 g/cm$^3$

Note that when the powder composition obtained as described above was dried at 20° C. for 72 hours, a powder composition having a loose bulk density of 0.5 g/cm$^3$ was obtained.

average particle diameter: 118 μm expansion ratio: ×1.3

As illustrated in FIG. 11, the powder composition obtained in Example 35 was in the form of powder.

Examples 36 to 38 employed lecithin (hydrophobic phospholipid) as the liquid component.

Example 36

After 9.9 g of powder-form powderizing agent A' and 0.1 g of SLP-Paste (manufactured by Tsuji Oil Mill Co., Ltd.) were placed into SV-110 (manufactured by Nichiden-Rika Glass Co., Ltd.), these were completely mixed at 20° C. Here, the amount of the liquid component used was 1% by mass relative to the total mass of the powder composition (powderizing agent A+liquid component).

The characteristics of the obtained powder composition were as follows.

loose bulk density: 0.3 g/cm$^3$ average particle diameter: 126 μm

Note that since the powder-form powderizing agent A' was used, the expansion ratio was not measured.

Figure 12:
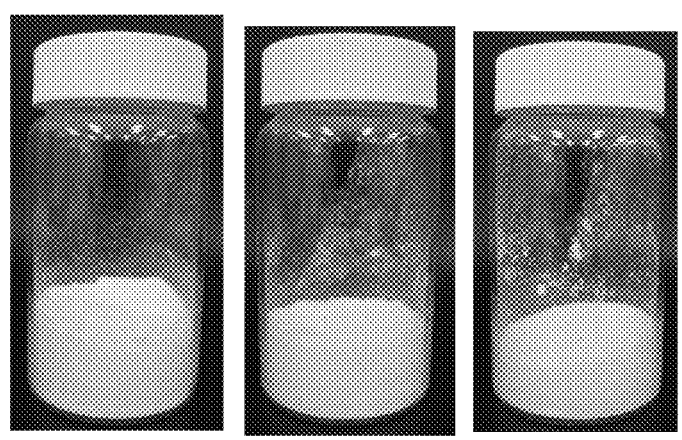
FIG. 12 is a view illustrating powder compositions obtained in Examples 36 to 38.

As illustrated in FIG. 12, the powder composition obtained in Example 36 was in the form of powder.

Example 37

After 9.5 g of powder-form powderizing agent A' and 0.5 g of SLP-Paste (manufactured by Tsuji Oil Mill Co., Ltd.) were placed into SV-110 (manufactured by Nichiden-Rika Glass Co., Ltd.), these were completely mixed at 20° C. Here, the amount of the liquid component used was 5% by mass relative to the total mass of the powder composition (powderizing agent A+liquid component).

The characteristics of the obtained powder composition were as follows.

loose bulk density: 0.3 g/cm$^3$ average particle diameter: 151 μm

Note that since the powder-form powderizing agent A' was used, the expansion ratio was not measured.

As illustrated in FIG. 12, the powder composition obtained in Example 37 was in the form of powder.

Example 38

After 9.0 g of powder-form powderizing agent A' and 1.0 g of SLP-Paste (manufactured by Tsuji Oil Mill Co., Ltd.) were placed into SV-110 (manufactured by Nichiden-Rika Glass Co., Ltd.), these were completely mixed at 20° C. Here, the amount of the liquid component used was 10% by mass relative to the total mass of the powder composition (powderizing agent A+liquid component).

The characteristics of the obtained powder composition were as follows.

loose bulk density: 0.3 g/cm$^3$ average particle diameter: 170 μm

Note that since the powder-form powderizing agent A' was used, the expansion ratio was not measured.

As illustrated in FIG. 12, the powder composition obtained in Example 38 was in the form of powder.

Table 1 summarizes the results of Examples described above.

TABLE 1

| | Name of Functional Material | Property of Liquid Component | Amount of Liquid Component Used (% by Mass) | Powderization Agent | Number of Carbon Atoms x | XXX-Type Triglyceride (% by Mass) | X2Y-Type Triglyceride (% by Mass) | Loose Bulk Density (g/cm3) | Average Particle Diameter (μm) | Expansion Ratio (Times) | Tempering Temperature/ Hours | Final Cooling Temperature/ Hours |
|---|---|---|---|---|---|---|---|---|---|---|---|---|
| Example 1 | Limonene | Hydrophobic | 1.0 | A | 10 | 94.0 | 5.2 | 0.3 | 121 | 3.9 | 10° C./ 0.5 Hours | 20° C./ 12 Hours |

TABLE 1-continued

| | Name of Functional Material | Property of Liquid Component | Amount of Liquid Component Used (% by Mass) | Powderization Agent | Number of Carbon Atoms x | XXX-Type Triglyceride (% by Mass) | X2Y-Type Triglyceride (% by Mass) | Loose Bulk Density (g/cm3) | Average Particle Diameter (μm) | Expansion Ratio (Times) | Tempering Temperature/ Hours | Final Cooling Temperature/ Hours |
|---|---|---|---|---|---|---|---|---|---|---|---|---|
| Example 2 | Limonene | Hydrophobic | 3.0 | A | 10 | 94.0 | 5.2 | 0.3 | 147 | 2.5 | 10° C./0.5 Hours | 20° C./12 Hours |
| Example 3 | Limonene | Hydrophobic | 5.0 | A | 10 | 94.0 | 5.2 | 0.4 | 198 | 1.6 | 10° C./0.5 Hours | 20° C./12 Hours |
| Example 4 | Vanillin | Hydrophobic | 1.0 | A | 10 | 94.0 | 5.2 | 0.3 | 116 | 4.0 | 10° C./0.5 Hours | 20° C./12 Hours |
| Example 5 | Vanillin | Hydrophobic | 3.0 | A | 10 | 94.0 | 5.2 | 0.3 | 139 | 2.7 | 10° C./0.5 Hours | 20° C./12 Hours |
| Example 6 | Vanillin | Hydrophobic | 5.0 | A | 10 | 94.0 | 5.2 | 0.3 | 140 | 2.9 | 10° C./0.5 Hours | 20° C./12 Hours |
| Example 7 | Orange Dye | Hydrophobic | 1.0 | A | 10 | 94.0 | 5.2 | 0.3 | 110 | 3.6 | 10° C./0.5 Hours | 20° C./12 Hours |
| Example 8 | Orange Dye | Hydrophobic | 5.0 | A | 10 | 94.0 | 5.2 | 0.3 | 121 | 3.5 | 10° C./0.5 Hours | 20° C./12 Hours |
| Example 9 | Orange Dye | Hydrophobic | 10.0 | A | 10 | 94.0 | 5.2 | 0.3 | 136 | 3.3 | 10° C./0.5 Hours | 20° C./12 Hours |
| Example 10 | Roasted Shrimp Oil | Hydrophobic | 1.0 | B | 12 | 93.1 | 5.8 | 0.3 | 149 | 3.9 | 28° C./1.0 Hour | 38° C./12 Hours |
| Example 11 | Roasted Shrimp Oil | Hydrophobic | 5.0 | B | 12 | 93.1 | 5.8 | 0.3 | 168 | 3.0 | 28° C./1.0 Hour | 38° C./12 Hours |
| Example 12 | Roasted Shrimp Oil | Hydrophobic | 10.0 | B | 12 | 93.1 | 5.8 | 0.3 | 170 | 2.9 | 28° C./1.0 Hour | 38° C./12 Hours |
| Example 13 | Onion Oil | Hydrophobic | 1.0 | B | 12 | 93.1 | 5.8 | 0.3 | 111 | 5.4 | 28° C./1.0 Hour | 38° C./12 Hours |
| Example 14 | Onion Oil | Hydrophobic | 5.0 | B | 12 | 93.1 | 5.8 | 0.3 | 137 | 3.9 | 28° C./1.0 Hour | 38° C./12 Hours |
| Example 15 | Onion Oil | Hydrophobic | 10.0 | B | 12 | 93.1 | 5.8 | 0.3 | 149 | 2.9 | 28° C./1.0 Hour | 38° C./12 Hours |
| Example 16 | Vitamin E | Hydrophobic | 1.0 | B | 12 | 93.1 | 5.8 | 0.3 | 107 | 5.1 | 28° C./1.0 Hour | 38° C./12 Hours |
| Example 17 | Vitamin E | Hydrophobic | 5.0 | B | 12 | 93.1 | 5.8 | 0.3 | 151 | 2.7 | 28° C./1.0 Hour | 38° C./12 Hours |
| Example 18 | Vitamin E | Hydrophobic | 10.0 | B | 12 | 93.1 | 5.8 | 0.3 | 190 | 1.7 | 28° C./1.0 Hour | 38° C./12 Hours |
| Example 19 | Lecithin | Hydrophobic | 1.0 | B | 12 | 93.1 | 5.8 | 0.3 | 123 | 4.7 | 28° C./1.0 Hour | 38° C./12 Hours |
| Example 20 | Lecithin | Hydrophobic | 5.0 | B | 12 | 93.1 | 5.8 | 0.3 | 119 | 4.9 | 28° C./1.0 Hour | 38° C./12 Hours |
| Example 21 | Lecithin | Hydrophobic | 10.0 | B | 12 | 93.1 | 5.8 | 0.3 | 130 | 4.3 | 28° C./1.0 Hour | 38° C./12 Hours |
| Example 22 | Lecithin | Hydrophobic | 20.0 | B | 12 | 93.1 | 5.8 | 0.3 | 176 | 2.6 | 28° C./1.0 Hour | 38° C./12 Hours |
| Example 23 | Lecithin | Hydrophobic | 30.0 | B | 12 | 93.1 | 5.8 | 0.4 | 214 | 1.7 | 28° C./1.0 Hour | 38° C./12 Hours |
| Example 24 | Shrimp Flavor | Hydrophilic | 1.0 | B | 12 | 93.1 | 5.8 | 0.3 | 163 | 3.1 | 28° C./1.0 Hour | 38° C./12 Hours |
| Example 25 | Shrimp Flavor | Hydrophilic | 5.0 | B | 12 | 93.1 | 5.8 | 0.4 | 188 | 1.4 | 28° C./1.0 Hour | 38° C./12 Hours |
| Example 26 | Shrimp Flavor | Hydrophilic | 10.0 | B | 12 | 93.1 | 5.8 | 0.5 | 184 | 1.0 | 28° C./1.0 Hour | 38° C./12 Hours |
| Example 27 | Orange Dye | Hydrophilic | 1.0 | B | 12 | 93.1 | 5.8 | 0.3 | 136 | 3.3 | 28° C./1.0 Hour | 38° C./12 Hours |
| Example 28 | Orange Dye | Hydrophilic | 5.0 | B | 12 | 93.1 | 5.8 | 0.3 | 110 | 3.7 | 28° C./1.0 Hour | 38° C./12 Hours |
| Example 29 | Orange Dye | Hydrophilic | 10.0 | B | 12 | 93.1 | 5.8 | 0.3 | 124 | 3.0 | 28° C./1.0 Hour | 38° C./12 Hours |
| Example 30 | Water | Hydrophilic | 100.0 | A | 10 | 94.0 | 5.2 | 0.8 (0.4) | 106 | 1.6 | — | 20° C./6 Hours |
| Example 31 | Water | Hydrophilic | 200.0 | A | 10 | 94.0 | 5.2 | 0.8 (0.4) | 104 | 1.3 | — | 20° C./6 Hours |
| Example 32 | Water | Hydrophilic | 300.0 | A | 10 | 94.0 | 5.2 | 0.9 (0.5) | 112 | 1.5 | — | 20° C./6 Hours |
| Example 33 | Cow's Milk | Hydrophilic | 100.0 | A | 10 | 94.0 | 5.2 | 0.9 (0.5) | 102 | 1.5 | — | 20° C./6 Hours |
| Example 34 | Cow's Milk | Hydrophilic | 200.0 | A | 10 | 94.0 | 5.2 | 0.9 (0.5) | 108 | 1.3 | — | 20° C./6 Hours |
| Example 35 | Cow's Milk | Hydrophilic | 300.0 | A | 10 | 94.0 | 5.2 | 0.9 (0.5) | 118 | 1.3 | — | 20° C./6 Hours |
| Example 36 | Lecithin | Hydrophobic | 1.0 | A' | 10 | 94.0 | 5.2 | 0.3 | 126 | — | — | — |

TABLE 1-continued

| Name of Functional Material | Property of Liquid Component | Amount of Liquid Component Used (% by Mass) | Powderization Agent | Number of Carbon Atoms x | XXX-Type Triglyceride (% by Mass) | X2Y-Type Triglyceride (% by Mass) | Loose Bulk Density (g/cm3) | Average Particle Diameter (μm) | Expansion Ratio (Times) | Tempering Temperature/ Hours | Final Cooling Temperature/ Hours |
|---|---|---|---|---|---|---|---|---|---|---|---|
| Example 37 | Lecithin | Hydrophobic | 5.0 | A' | 10 | 94.0 | 5.2 | 0.3 | 151 | — | — | — |
| Example 38 | Lecithin | Hydrophobic | 10.0 | A' | 10 | 94.0 | 5.2 | 0.3 | 170 | — | — | — |

INDUSTRIAL APPLICABILITY

The present invention is applicable to various fields of, for example, foods, pharmaceuticals, agriculture, and industry.

The invention claimed is:

1. A powderizing agent for a liquid component, wherein the powderizing agent contains an oil and/or fat composition, and
when a total triglyceride content is set to 100% by mass, the oil and/or fat composition contains
65 to 99% by mass of one or more types of XXX-type triglycerides having fatty acid residues X, each with x carbon atoms, at positions 1 to 3 and
35 to 1% by mass of one or more types of X2Y-type triglycerides each having a fatty acid residue Y with y carbon atoms in place of one of the fatty acid residues X of the XXX-type triglyceride,
x, the number of carbon atoms, is an integer selected from 8 to 20,
y, the number of carbon atoms, is each independently an integer selected from x+2 to x+12 and satisfies y≤22, and
the liquid component is a liquid at 20° C.

2. The powderizing agent according to claim 1, wherein the oil and/or fat composition is in a powder form.

3. The powderizing agent according to claim 1, wherein the liquid component contains a hydrophobic substance.

4. The powderizing agent according to claim 1, wherein the liquid component is a solution of a hydrophobic substance.

5. The powderizing agent according to claim 1, wherein the liquid component is an emulsion of a hydrophobic substance.

6. The powderizing agent according to claim 3, wherein the hydrophobic substance is selected from the group consisting of flavors, dyes, vitamins, lipids, and mixtures thereof.

7. The powderizing agent according to claim 1, wherein the liquid component contains a hydrophilic substance.

8. The powderizing agent according to claim 1, wherein the liquid component is a solution of a hydrophilic substance.

9. The powderizing agent according to claim 1, wherein the liquid component is an emulsion of a hydrophilic substance.

10. The powderizing agent according to claim 7, wherein the hydrophilic substance is selected from the group consisting of flavors, dyes, vitamins, and mixtures thereof.

11. The powderizing agent according to claim 1, wherein the liquid component is a liquid form food.

12. The powderizing agent according to claim 11, wherein the liquid form food is selected from the group consisting of cow's milk, wines, fruit juices, stock, and yogurts.

13. A method of producing a powder composition, comprising:
a mixing step of mixing a powderizing agent and a liquid component,
wherein the powderizing agent contains an oil and/or fat composition, and
when a total triglyceride content is set to 100% by mass, the oil and/or fat composition contains
65 to 99% by mass of one or more types of XXX-type triglycerides having fatty acid residues X, each with x carbon atoms, at positions 1 to 3 and
35 to 1% by mass of one or more types of X2Y-type triglycerides each having a fatty acid residue Y with y carbon atoms in place of one of the fatty acid residues X of the XXX-type triglyceride,
x, the number of carbon atoms, is an integer selected from 8 to 20,
y, the number of carbon atoms, is each independently an integer selected from x+2 to x+12 and satisfies y≤22, and
wherein the liquid component is a liquid at 20° C.

14. The production method according to claim 13, further comprising a cooling step of cooling a mixture of the powderizing agent and the liquid component.

15. The production method according to claim 14, wherein
a seeding process, a tempering process, and/or a pre-cooling process are further performed between the mixing step and the cooling step.

16. The production method according to claim 13, wherein
the liquid component contains a hydrophobic substance, and
an amount of the liquid component used is 0.1 to 30% by mass relative to a total mass of the powder composition.

17. The production method according to claim 13, wherein
the liquid component contains a hydrophilic substance, and
an amount of the liquid component used is 0.1 to 300% by mass relative to a total mass of the powderizing agent.

18. A powder composition comprising the powderizing agent according to claim 1 and a liquid component, wherein the liquid component is a liquid at 20° C.

19. A food and/or beverage comprising the powder composition according to claim 18.

20. The production method according to claim 13, wherein
the oil and/or fat composition is in a powder form.

21. The production method according to claim 13, wherein
the liquid component contains a hydrophobic substance.

22. The production method according to claim 13, wherein the liquid component is a solution of a hydrophobic substance.

23. The production method according to claim 13, wherein the liquid component is an emulsion of a hydrophobic substance.

24. The production method according to claim 21, wherein the hydrophobic substance is selected from the group consisting of flavors, dyes, vitamins, lipids, and mixtures thereof.

25. The production method according to claim 13, wherein the liquid component contains a hydrophilic substance.

26. The production method according to claim 13, wherein the liquid component is a solution of a hydrophilic substance.

27. The production method according to claim 13, wherein the liquid component is an emulsion of a hydrophilic substance.

28. The production method according to claim 25, wherein the hydrophilic substance is selected from the group consisting of flavors, dyes, vitamins, and mixtures thereof.

29. The production method according to claim 13, wherein the liquid component is a liquid form food.

30. The production method according to claim 29, wherein the liquid form food is selected from the group consisting of cow's milk, wines, fruit juices, stock, and yogurts.

\* \* \* \* \*